United States Patent
Holgersson et al.

(10) Patent No.: US 7,658,919 B2
(45) Date of Patent: Feb. 9, 2010

(54) COMPOSITIONS AND METHODS FOR INHIBITING H. PYLORI ADHESION AND INFECTION

(75) Inventors: Jan Holgersson, Huddinge (SE); Jining Liu, Stockholm (SE); Anki Gustafsson, Stockholm (SE); Jonas Lofling, Stockholm (SE)

(73) Assignee: Recopharma AB, Stockholm (SE)

( * ) Notice: Subject to any disclaimer, the term of this patent is extended or adjusted under 35 U.S.C. 154(b) by 231 days.

(21) Appl. No.: 11/251,140

(22) Filed: Oct. 14, 2005

(65) Prior Publication Data

US 2006/0177463 A1 Aug. 10, 2006

Related U.S. Application Data

(60) Provisional application No. 60/619,379, filed on Oct. 14, 2004, provisional application No. 60/720,103, filed on Sep. 22, 2005.

(51) Int. Cl.
C07K 19/00 (2006.01)

(52) U.S. Cl. .................... 424/134.1; 530/395

(58) Field of Classification Search .............. None
See application file for complete search history.

(56) References Cited

U.S. PATENT DOCUMENTS

| | | | |
|---|---|---|---|
| 5,225,538 A | 7/1993 | Capon et al. | 530/387.3 |
| 5,428,130 A | 6/1995 | Capon et al. | 530/350 |
| 5,455,165 A | 10/1995 | Capon et al. | 435/64.7 |
| 5,514,582 A | 5/1996 | Capon et al. | 435/252.3 |
| 5,516,964 A | 5/1996 | Umansky et al. | 585/751 |
| 5,714,147 A | 2/1998 | Capon et al. | 424/178.1 |
| 6,136,310 A | 10/2000 | Hanna et al. | 424/154.1 |
| 7,355,017 B2* | 4/2008 | Lofling et al. | 530/391.1 |
| 2003/0073822 A1* | 4/2003 | Lofling et al. | 530/391.1 |

FOREIGN PATENT DOCUMENTS

| WO | WO 03/010201 A2 | 2/2003 |
|---|---|---|
| WO | WO 03/089450 A2 | 10/2003 |

OTHER PUBLICATIONS de Vries et al. (Glycobiol., 11:119R-128R, 2001).*
Shiraishi et al. (J. Biol. Chem., 276:3498-3507, 2001).*
Lofling et al. Abstract No. 627.4, FASEB J., vol. 17, No. 4-5, Mar. 2003.*
Lofling et al. Glycobiol., 12:173-182, 2002.*
Amado et al., "A Family of Human β3-Galactosyltransferases", J. Biol. Chem., 273(21):12770-12778 (1998).
Amano et al., "Expression of the H Type 1 Blood Group Antigen during Enterocytic Differentiation of Caco-2 Cells", J. Biol. Chem., 274(30):21209-21216 (1999).
Appelmelk et al., "Cutting Edge: Carbohydrate Profiling Identifies New Pathogens That Interact with Dendritic Cell-Specific ICAM-3-Grabbing Nonintegrin on Dendritic Cells", J. Immunol., 170:1635-1639 (2003).

Bergman et al., Helicobacter pylori Modulates the T Helper Cell 1/T Helper Cell 2 Balance through Phase-variable Interaction between Lipopolysaccharide and DC-SIGN, J. Exp. Med., 200(8):979-990 (2004).
Cole et al., "Identification, expression analysis, and mapping of B3galt6, a putative galactosyl transferase gene with similarity to Drosophila brainiac", Mamm. Genome, 12:177-179 (2001).
Falk et al., "Expression of a human α-1,3/4-fucosyltransferase in the pit cell lineage of FVB/N mouse stomach results in production of Le$^b$-containing glycoconjugates: A potential transgenic mouse model for studying Helicobacter pylori infection" Proc. Natl. Acad. Sci. U.S.A., 92:1515-1519 (1995).
GenBank Accession No. AAH12725, Jul. 15, 2006, 3 pages.
GenBank Accession No. AAH26238, Jul. 15, 2006, 3 pages.
GenBank Accession No. AJ417832, Oct. 21, 2008, 4 pages.
GenBank Accession No. BAA13941, Oct. 5, 2006, 2 pages.
GenBank Accession No. BAA13942, Oct. 5, 2006, 2 pages.
GenBank Accession No. BC012725, Jul. 15, 2006, 4 pages.
GenBank Accession No. BC026238, Jul. 15, 2006, 3 pages.
GenBank Accession No. CAD10625, Oct. 21, 2008, 3 pages.
GenBank Accession No. D89324, Oct. 5, 2006, 3 pages.
GenBank Accession No. D89325, Oct. 5, 2006, 3 pages.
GenBank Accession No. NM_000149, Mar. 22, 2009, 6 pages.
GenBank Accession No. NM_000511, Apr. 5, 2009, 6 pages.
GenBank Accession No. NM_009151, Apr. 5, 2009, 5 pages.
GenBank Accession No. NM_016888, Feb. 1, 2009, 5 pages.
GenBank Accession No. NM_053288, Jan. 13, 2008, 4 pages.
GenBank Accession No. NM_144677, Feb. 1, 2009, 7 pages.
GenBank Accession No. NM_145650, Dec. 21, 2008, 5 pages.
GenBank Accession No. NM_198955, Feb. 1, 2009, 7 pages.
GenBank Accession No. NP_000140, Mar. 22, 2009, 4 pages.
GenBank Accession No. NP_000502, Apr. 5, 2009, 4 pages.
GenBank Accession No. NP_058584, Feb. 1, 2009, 3 pages.
GenBank Accession No. NP_653278, Feb. 1, 2009, 4 pages.
GenBank Accession No. NP_663625, Dec. 21, 2008, 3 pages.
GenBank Accession No. NP_945193, Feb. 1, 2009, 4 pages.
GenBank Accession No. NP_000598, Apr. 12, 2009, 4 pages.
GenBank Accession No. NP_0033177, Apr. 5, 2009, 4 pages.
GenBank Accession No. NP_044570, Apr. 15, 2009, 3 pages.
GenBank Accession No. XM_006867, Aug. 1, 2002, 3 pages.
GenBank Accession No. XM_140694, Oct. 8, 2002, 2 pages.
GenBank Accession No. XP_006867, Aug. 1, 2002, 2 pages.
GenBank Accession No. XP_140694, Oct. 8, 2002, 2 pages.

(Continued)

Primary Examiner—Robert B Mondesi
Assistant Examiner—Brian J Gangle
(74) Attorney, Agent, or Firm—Mintz, Levin, Cohn, Ferris, Glovsky and Popeo, P.C.; Ivor R. Elrifi; Cynthia A. Kozakiewicz

(57) ABSTRACT

The present invention provides compositions and methods for treating or preventing bacterial infections. Also provide by the invention are genetically modified cell expressing Lewis$^b$ carbohydrate epitope.

12 Claims, 9 Drawing Sheets

OTHER PUBLICATIONS

Gerhard et al., "Clinical relevance of the *Helicobacter pylori* gene for blood-group antigen-binding adhesion", *Proc. Natl. Acad. Sci. U.S.A.*, 96(22):12778-12783 (1999).

Guruge et al., "Epithelial attachment alters the outcome of *Helicobacter pylori* infection", *Proc. Natl. Acad. Sci. U.S.A.*, 95:3925-3930 (1998).

Holgersson et al., "Glycosyltransferases involved in type 1 chain and Lewis antigen biosynthesis exhibit glycan and core chain specificity", *Glycobiol.*, Abstract #133, 15(11):1219 (2005).

Ilver et al., "*Helicobacter pylori* Adhesin Binding Fucosylated Histo-Blood Group Antigens Revealed by Retagging", *Science*, 279:373-377 (1998).

Isshiki et al., "Cloning, Expression, and Characterization of a Novel UDP-galactose:β-N-Acetylglucosamine β1,3-Galactosyltransferase (β3Gal-T5) Responsible for Synthesis of Type 1 Chain in Colorectal and Pancreatic Epithelia and Tumor Cells Derived Therefrom", *J. Biol. Chem.*, 274(18):12499-12507 (1999).

Iwai et al., "Molecular Cloning and Characterization of a Novel UDP-GlcNAc:GalNAc-peptide β1,3-*N*-Acetylglucosaminyltransferase (β3Gn-T6), an Enzyme Synthesizing the Core 3 Structure of *O*-Glycans" *J. Biol. Chem.*, 277(15):12802-12809 (2002).

Kelly et al., "Sequence and Expression of a Candidate for the Human Secretor Blood Group α(1,2)Fucosyltransferase Gene (*FUT2*)", *J. Biol. Chem.*, 270(9):4640-4649 (1995).

Kolbinger et al., "Cloning of a Human UDP-galactose:2-Acetamido-2-deoxy-D-glucose 3β-Galactosyltransferase Catalyzing the Formation of Type 1 Chains", *J. Biol. Chem.*, 273(1):433-440 (1998).

Kotani et al., "Knockout of mouse β1,4-galactosyltransferase-1 gene results in a dramatic shift of outer chain moieties of N-glycans from type 2 to type 1 chains in hepatic membrane and plasma glycoproteins", *Biochem. J.*, 357:827-834 (2001).

Kukowska-Latallo et al., "A cloned human cDNA determines expression of a mouse stage-specific embryonic antigen and the Lewis blood group α(1,3/1,4)fucosyltransferase", *Genes Dev.*, 4:1288-1303 (1990).

Löfling et al., "Absorption of anti-blood group A antibodies on P-selectin glycoprotein ligand-1/immunoglobulin chimeras carrying blood groupA determinants: core saccharide chain specificity of the *Se* and *H* gene encoded α1,2 fucosyltransferases in different host cells", *Glycobiology*, 12(3):173-182 (2002).

Mahdavi et al., *Helicobacter pylori* SabA Adhesion in Persistent Infection and Chronic Inflammation, *Science*, 297:573-578 (2002).

Mare et al., "Suppression of α1,3galactosyltransferase β3Gal-T5 in cancer cells reduces sialyl-Lewis a and enhances poly N-acetyllactosamines and sialyl-Lewis x on O-glycans", *Eur. J. Biochem.*, 271:186-194 (2004).

Mitoma et al., "Extended core 1 and core 2 branched O-glycans differentially modulate Sialyl Lewis x-type L-selectin ligand activity", *J. Biol. Chem.*, 278(11):9953-9961 (2003).

Narimatsu et al., "Genetic Evidence for the Lewis Enzyme, Which Synthesizes Type-1 Lewis Antigens in Colon Tissue, and Intracellular Localization of the Enzyme", *Cancer Res.*, 56:330-338 (1996).

Narimatsu et al., "*Lewis* and *Secretor* Gene Dosages Affect CA 19-9 and DU-PAN-2 Serum Levels in Normal Individuals and Colorectal Cancer Patients", *Cancer Res.*, 58:512-518 (1998).

Prieto et al., "Expression of Human H-type α1,2-Fucosyltransferase Encoding for Blood Group H(O) Antigen in Chinese Hamster Ovary Cells", *J. Biol. Chem.*, 272(4):2089-2097 (1997).

Prinz et al., "Key Importance of the *Helicobacter pylori* Adherence Factor Blood Group Antigen Binding Adhesin during Chronic Gastric Inflammation", *Cancer Res.*, 61:1903-1909 (2001).

Rad et al., "The *Helicobacter pylori* Blood Group Antigen-Binding Adhesin Facilitates Bacterial Colonization and Augments a Nonspecific Immune Response", *J. Immunol.*, 168:3033-3041 (2002).

Takahashi et al., "A Novel In Vitro Infection Model of *Helicobacter pylori* Using Mucin-Producing Murine Gastric Surface Mucous Cells", *Helicobacter*, 9(4):302-312 (2004).

Wang et al., "Lewis antigens in *Helicobacter pylori*: biosynthesis and phase variation", *Mol. Microbiol.* 36(6):1187-1196 (2000).

Zhou et al., "Molecular cloning of a human UDP-galactose:GlcNAcβ1,3GalNAcβ1,3 galactosyltransferase gene encoding an O-linked core3-elongation enzyme", *Eur. J. Biochem.*, 263:571-576 (1999).

\* cited by examiner

CHO

1C5

2C2

```
                        SEQUENCE LISTING

<160> NUMBER OF SEQ ID NOS: 4

<210> SEQ ID NO 1
<211> LENGTH: 33
<212> TYPE: DNA
<213> ORGANISM: artificial sequence
<220> FEATURE:
<223> OTHER INFORMATION: synthetic primer

<400> SEQUENCE: 1
cgcgggaagc ttaccatggc ttttccctgc cgc                              33

<210> SEQ ID NO 2
<211> LENGTH: 30
<212> TYPE: DNA
<213> ORGANISM: artificial sequence
<220> FEATURE:
<223> OTHER INFORMATION: synthetic primer

<400> SEQUENCE: 2
cgcgggtcta gatcaggaga cccggtgtcc                                  30

<210> SEQ ID NO 3
<211> LENGTH: 33
<212> TYPE: DNA
<213> ORGANISM: artificial sequence
<220> FEATURE:
<223> OTHER INFORMATION: synthetic primer

<400> SEQUENCE: 3
cgcgggaagc ttaccatggc tttcccgaag atg                              33

<210> SEQ ID NO 4
<211> LENGTH: 35
<212> TYPE: DNA
<213> ORGANISM: artificial sequence
<220> FEATURE:
<223> OTHER INFORMATION: synthetic primer

<400> SEQUENCE: 4
cgcgggcggc cgctttagac aggcggacaa tcttc                            35
```

COMPOSITIONS AND METHODS FOR INHIBITING *H. PYLORI* ADHESION AND INFECTION

RELATED APPLICATIONS

This application claims priority to U.S. Ser. No. 60/619,379 filed Oct. 14, 2004 and U.S. Ser. No. 60/720,103 filed Sep. 22, 2005, the contents of each are incorporated herein by reference in their entireties.

FIELD OF THE INVENTION

The invention relates to generally to compositions and methods for treating or preventing *H. pylori* infection and more particularly to compositions including fusion polypeptides and cell lines comprising carbohydrate epitopes that mediate *H. pylori* adhesion.

BACKGROUND OF THE INVENTION

Humans, are continuously exposed to different pathogens such as viruses and bacteria. Some of these are species-specific while others can colonize and infect a variety of species. Host cell adhesion of pathogens is a prerequisite for most infections and for many bacteria, viruses and bacterial toxins, binding is mediated by lectins that recognize and bind to different carbohydrate epitopes. Today, the most common treatment for bacterial infections is the use of various antibiotics; a treatment that can be complicated by the occurrence of pathogenic strains resistant to commonly used antibiotics and adverse effects including allergy.

SUMMARY OF THE INVENTION

The invention is based in part on the discovery that carbohydrate epitopes that mediate *H. Pylori* adhesion and infection can be specifically expressed at high density and by different core saccharides chains on mucin-type protein backbones. The polypeptides, are referred to herein as HP fusion polypeptides.

In one aspect, the invention provides a fusion polypeptide that includes a first polypeptide that is glycosylated by a α 1,¾ fucosyltransferase (FUT3), an α 1,2 fucosyltransferase (FUT2) and a β 1,3 galactosyltransferase operably linked to a second polypeptide. Optionally, the first polypeptide is further glycosylated by a β 1,3, N-acetylglucosaninyltransferase to add O-linked glycans.

The first polypeptide is, for example, a mucin polypeptide such as PSGL-1 or portion thereof. Preferably, the mucin polypeptide is the extracellular portion of PSGL-1. Alternatively, the first polypeptide is an alpha glycoprotein such as alpha 1-acid glycoprotein (i.e., orosomuciod or AGP) or portion thereof.

The second polypeptide comprises at least a region of an immunoglobulin polypeptide. For example, the second polypeptide comprises a region of a heavy chain immunoglobulin polypeptide. Alternatively, the second polypeptide comprises the FC region of an immunoglobulin heavy chain.

The HP fusion polypeptide is a mutimer. Preferably, the HP fusion polypeptide is a dimer.

Also included in the invention is a nucleic acid encoding an HP fusion polypeptide, as well as a vector containing HP fusion polypeptide-encoding nucleic acids described herein, and a cell containing the vectors or nucleic acids described herein. Alternatively, the vector further contains a nucleic acid encoding an α 1,¾ fucosyltransferase (FUT3), an α 1,2 fucosyltransferase (FUT2) and a β 1,3 galactosyltransferase. Optionally, the vector further contains a nucleic acid encoding a β 1,3, N-acetylglucosaminyltransferase.

In another aspect, the invention provides a method of inhibiting (e.g., decreasing) bacterial or bacterial toxin adhesion to a cell. Adhesion is inhibited by contacting the cell with the HP fusion polypeptide. The cell is contacted in vivo, in vitro, or ex vivo. The cell is for example a gastric cell. The invention also features methods of preventing or alleviating a symptom of an microbial infection or a disorder associated with a microbial infection in a subject by identifying a subject suffering from or at risk of developing a bacterial infection and administering to the subject a HP fusion polypeptide. The bacteria, e.g., *Helicobacter pylori*.

The subject is a mammal such as human, a primate, mouse, rat, dog, cat, cow, horse, pig. The subject is suffering from or at risk of developing a bacterial infection or a disorder associated with a bacterial infection. A subject suffering from or at risk of developing a bacerial infection or a disorder associated with a bacterial infection is identified by methods known in the art, e.g., gross examination of tissue or detection of microbial colonization in the associated in tissue or blood. Symptoms of a microbial infection or a disorder associated with a microbial infection include abdominal pain, nausea or vomiting. A subject suffering from a bacterial infection or a disorder associated with a bacterial infection, such as *Helicobacter pylori*, is identified blood, breath or stool tests known in the art.

Also included in the invention are pharmaceutical compositions that include the HP fusion polypeptides.

The invention further provides a gentetically modified cell and cell cultures expressing carbohydrate epitopes that mediate *H. pylori* adhesion, e.g. $Le^b$. The cells are referred to herein as "LBC" cells. The cells are genetically modified with a nucleic acid encoding a β 1,3, N-acetylglucosaminyltransferase gene (βGn-T6) a β1,3 galactosyltransferase (β3Gal-T5) gene, a α1,¾ fucosyltransferase gene (Fuc-T3) and a α1,2 fucosyltransferase gene (FucT-2).

An inhibitor or enhancer of the *H. pylori* interaction is identified by contacting a LBC with a *H. pylori* bacterium and a test compound under conditions where LBC and *H. pylori* bacterium are capable of forming a complex and the amount of complex formation is determined. A decrease in the amount of complex formation in the presence of the test compound compared to the absence of the test compound indicates that the test compound in as inhibitor of *H. pylori* adhesion. In contrast, an increase in the amount of complex formation in the presence of the test compound compared to the absence of the test compound indicates that the test compound in as enhancer of *H. pylori* adhesion.

The invention also provide a method of identifying an agent that binds a $Le^b$ carbohydrate epitope by contacting a LBC with a $Le^b$ epitope binding agent, e.g., *H. pylori* bacterium with a test agent and determining whether the agent binds the LBC, e.g. forms a complex. A decrease in the amount of complex formation in the presence of the test compound compared to the absence of the test compound indicates that the test compound binds a $Le^b$ carbohydrate epitope.

The invention also includes an modulator compounds identified according to these screening methods, and a pharmaceutical composition which includes the modulators.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
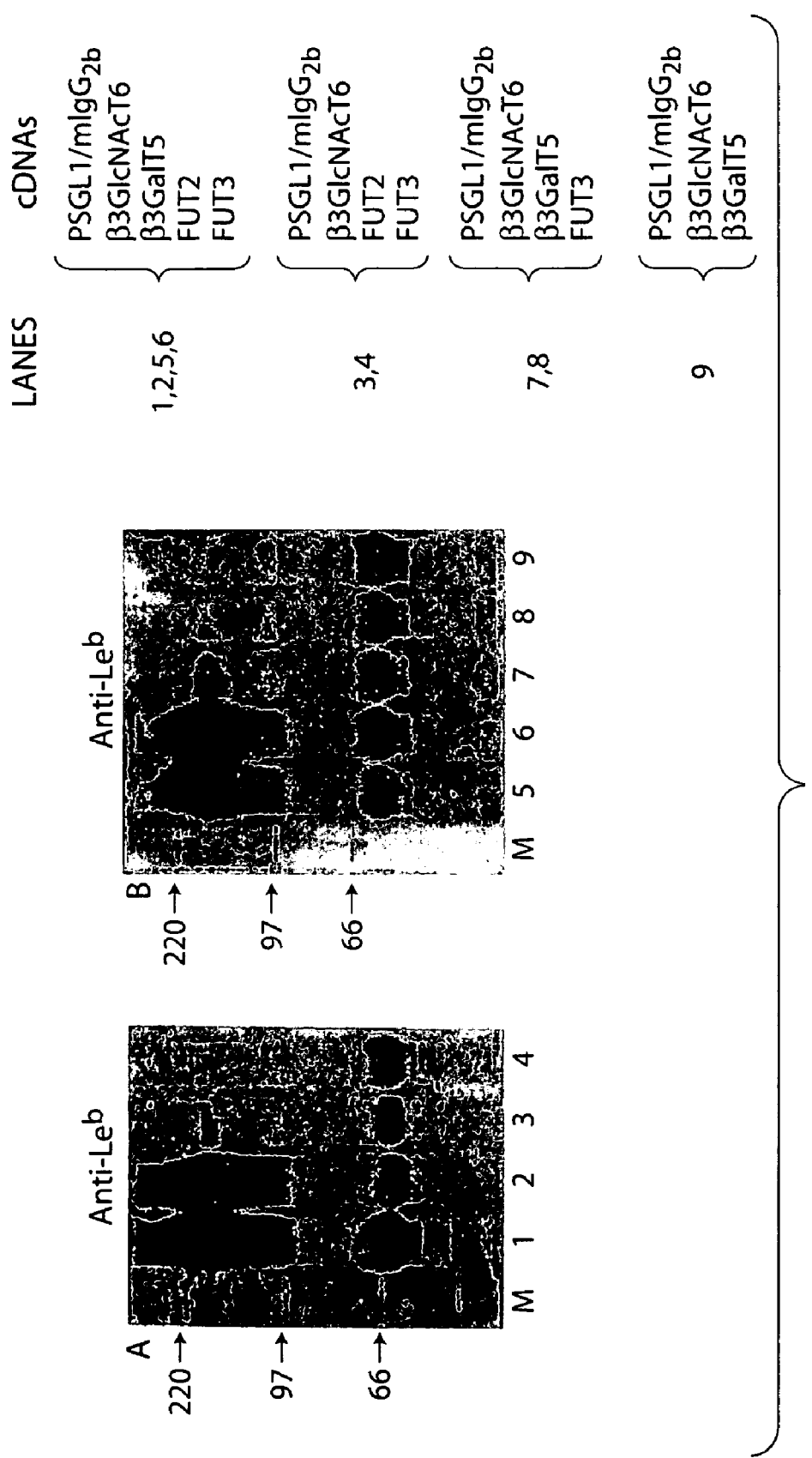
FIG. 1 is a photograph of a Western blot showing luminescence from the binding of monoclonal anti-Le$^b$ antibodies. Lanes 1, 2, 5 and 6 contain elutions obtained from lysates from CHO cells expressing β3GlcNAcT6, βGalT5, FUT2, and FUT3 which were incubated with agarose beads coupled to anti-mouse IgG$_{2b}$. Lanes 3 and 4 contain elutions obtained from lysates CHO cells expressing β3GlcNAcT6, βGalT5, and FUT3 which were incubated with agarose beads coupled to anti-mouse IgG$_{2b}$. Lanes 7 and 8 contain elutions obtained from lysates from CHO cells expressing β3GlcNAcT6, FUT2, and FUT3 which were incubated with agarose beads coupled to anti-mouse IgG$_{2b}$. Lane 9 contains elutions obtained from lysates from CHO cells expressing β3GlcNAcT6 and βGalT5 which were incubated with agarose beads coupled to anti-mouse IgG$_{2b}$.

The invention is based in part in the discovery that carbohydrate epitopes that mediate Helicobacter pylo I (H. pylori) adhesion can be specifically expressed at high density on glycoproteins, e.g., mucin-type and alpha glycoprotein protein backbones. This higher density of carbohydrate epitopes results in an increased valancy and affinity compared to monovalent oligosaccharides. The invention further provides a gentetically modified cell expressing carbohydrate epitopes that mediate H. pylori adhesion that are useful in identifying compounds that inhibit H. pylori adhesion.

The carbohydrate antigens, sialyl Lewis (e.g. Le$^a$, Leb$^a$, Le$^x$, Le$^y$), are ligands for cell adhesion molecules. The human gastric pathogen, Helicobacter pylori express Lewis antigens on there surface lipopolysaccharide (LPS) O-antigen.

H. pylori is a gram-negative bacterium that resides in more than half of the world population It resides in the gastric mucosa or adheres to the epithelial cells lining the stomach. H. pylori is associated with the development of peptic ulcer disease, mucosa-associated lymphoid-tissue (MALT) lymphoma and gastric adenocarcinoma. The reason why not all infected patients develop stomach cancer is unknown. The binding properties of H. pylori to different glycoconjugates have been extensively studied, and a number of binding specificities identified. Two of these are the carbohydrate epitopes Lewis (Le)$^b$ and sialyl-Lewis (Le)$^x$.

In order to colonize its host the bacterium needs to attach to the epithelium. Many different receptors for H. pylori have been described. Most of them are carbohydrates and two are considered especially important, Lewis B (Le$^b$) and Sialyl-Lewis X (SLe$^x$). The adhesins mediating this attachment, BabA (1) and SabA (2), respectively, have recently been cloned. It has been shown that the ability of H. pylori to bind to Le$^b$ is a major risk factor for developing malignant disease (3-5) and a correlation between binding to SLe$^x$ and gastric cancer has been suggested (2). Several models have been used to study the attachment of *H. pylori*. One successful strategy has been to engineer the carbohydrate receptors in mice, which normally are not susceptible to infection by *H. pylori*. In this model, it was shown that binding to Le$^b$ did not increase the number of attaching bacteria, but the severity of the inflammation (6).

It has been a long-standing prevailing idea is to use carbohydrate-based inhibitors of microbial adhesion as a means of treating and/or preventing infectious diseases. However, to date, this strategy has been proven insufficient in human clinical trials. A potential explanation for the lack of efficacy of carbohydrate-based monovalent inhibitors is the usually low affinity with which a carbohydrate ligand binds its receptor.

In contrast, the present invention provides recombinant, mucin- and α$_1$-acid glycoprotein-based proteins which are heavily substituted with blood group Le$^b$ epitopes on their O- and N-linked glycans, respectively. Further, the invention demonstratrates, unkike previous work with monovalent carbohyraye inhibitor, that *H. pylori* strains with a defined carbohydrate binding specificity adhere to multivalent Le$^b$-substituted proteins of the invention.

Moreover, there are currently no cell lines available that have the desired properties for adhesion studies in vitro to defined carbohydrates such as Lewis b (Le$^b$): HT-29, AGS, Kato III, HuTu-80 and Hep-2 are all cells that have been used in adhesion experiments with *H. pylori*. A recent report by Takahashi et al (7) described the use of a murine gastric cell line made to express mucins as a model system for *H. pylori*. All these cell lines, however, are poorly characterized with regard to their carbohydrate phenotypes. Furthermore, cell-lines of gastrointestinal origin also express endogenous mucins, both membrane-bound and secreted, making it more difficult to get an overview of possible receptors. Thus, a need exists for a stable cell line for in vitro *H. pylori* adhesion studies and to identify inhibitors of bacterial adhesion and infection. Thus, in a further aspect, the invention provides gentetically modified cells expressing the carbohydrate antigen Le$^b$.

The present invention demonstrates that by stably expressing β3Gal-T5, βGn-T6, Fuc-T3 and FucT-2, it is possible to make Le$^b$ on O-glycans, N-glycans and glycolipids in CHO-K1-cells. Furthermore, using defined *H. pylori*-strains, it was demonstrated that *H. pylori* attachment to the cells is BabA specific and that it requires Le$^b$. The cells expressing Le$^b$ can be used to produce recombinant proteins carrying the epitope, as shown by transient expression of different recombinant proteins and for adhesion experiments, e.g., with *H. pylori*. Interestingly, one clone, 1C5, which express Le$^b$ on O-glycans, but not on N-glycans or glycolipids. The other clone, 2C2, expresses Le$^b$ on O- and N-glycans as well as on glycolipids. There is also an interesting difference in cell surface staining between the two Le$^b$-expressing clones in that 1C5 does not express Le$^Y$, whereas 2C2 does. Despite these differences in glycan repertoire, no clear difference between these clones in terms of *H. pylori* adherence was detected. These cells are useful as an in vitro model for molecular and cell biological studies on host cell- as well as bacterial responses to *H. pylori* attachment.

The invention provides glycoprotein-immunoglobulin fusion proteins (refered to herein as "HP fusion protein or HP fusion peptides") containing multiple sialyl-lewis epitopes, that are useful in blocking (i.e., inhibiting) the adhesion interaction between a bacteria, or a bacterial toxin and a cell. Preferably, the HP fusion proteins contain the Le$^b$ epitope The HP fusion protein inhibits 10%, 20%, 30, 40%, 50%, 60%, 70%, 80%, 90%, 95%, 98% or 100% of the bacteria, or a bacterial toxin adhesion to a cell. For example, the HP fusion proteins are useful in inhibiting *H. pylori* adhesion to gastric mucosa.

The HP fusion peptide is more efficient on a carbohydrate molar basis in inhibiting microbial or toxin adhesion as compared free saccharides of wild type sialyl-Le. The HP fusion peptide inhibits 2, 4, 10, 20, 50, 80, 100 or more-fold greater number of bacteria, or a bacterial toxin as compared to an equivalent amount of free saccharides of wild type sialyl-Le determinants.

The HP fusion proteins of the invention carries an epitope specific for a sialyl Lewis antigen. For example, the HP fusion protein carries either the Le$^a$ epitope, the Le$^b$ epitope, Le$^x$ or the Le$^y$ epitope. Preferably, the HP fusion protein carries the Le$^b$ epitope. Alternatively, the HP fusion carries two sialyl Lewis antigens. For example, the HP fusion protein carries both the Le$^x$ and Le$^b$ epitope. Alternatively, the HP fusion protein carries all four epitopes ( i.e., A, B, X and Y). The sialyl Lewis antigens are O-linked. Alternatively, the sialy Lewis antigens are N-linked. Optionally, the fusion protein contains sialyl Lewis antigens are O-linked and N-linked.

Fusion Polypeptides

In various aspects the invention provides fusion proteins that include a first polypeptide containing at least a portion of a glycoprotein, e.g., a mucin polypeptide or an alpha-globulin polypeptide, operatively linked to a second polypeptide. As used herein, a "fusion protein" or "chimeric protein" includes at least a portion of a glycoprotein polypeptide operatively linked to a non-mucin polypeptide.

A "mucin polypeptide" refers to a polypeptide having a mucin domain. The mucin polypeptide has one, two, three, five, ten, twenty or more mucin domains. The mucin polypeptide is any glycoprotein characterized by an amino acid sequence substituted with O-glycans. For example, a mucin polypeptide has every second or third amino acid being a serine or threonine. The mucin polypeptide is a secreted protein. Alternatively, the mucin polypeptide is a cell surface protein.

Mucin domains are rich in the amino acids threonine, serine and proline, where the oligosaccharides are linked via N-acetylgalactosamine to the hydroxy amino acids (O-glycans). A mucin domain comprises or alternatively consists of an O-linked glycosylation site. A mucin domain has 1, 2, 3, 5, 10, 20, 50, 100 or more O-linked glycosylation sites. Alternatively, the mucin domain comprises or alternatively consists of a N-linked glycosylation site. A mucin polypeptide has 50%, 60%, 80%, 90%, 95% or 100% of its mass due to the glycan. A mucin polypeptide is any polypeptide encode for by a MUC genes (i.e., MUC1, MUC2, MUC3, etc.) Alternatively, a mucin polypeptide is P-selectin glycoprotein ligand 1 (PSGL-1), CD34, CD43, CD45, CD96, GlyCAM-1, MAd-CAM or red blood cell glycophorins. Preferably, the mucin is PSGL-1.

An "alpha-globulin polypeptide" refers to a serum glycoprotein. Alpha-globulins include for example, enzymes produced by the lungs and liver, and haptoglobin, which binds hemoglobin together. An alpha-globulin is an alpha$_1$ or an alpha$_2$ globulin. Alpha$_1$ globulin is predominantly alpha$_1$ antitrypsin, an enzyme produced by the lungs and liver. Alpha$_2$ globulin, which includes serum haptoglobin, is a protein that binds hemoglobin to prevent its excretion by the kidneys. Other alphaglobulins are produced as a result of inflammation, tissue damage, autoimmune diseases, or certain cancers. Preferably, the alpha-globulin is alpha-1-acid glycoprotein (i.e., orosomucoid.

A "non-mucin polypeptide" refers to a polypeptide of which at least less than 40% of its mass is due to glycans.

Within a HP fusion protein of the invention the mucin polypeptide corresponds to all or a portion of a mucin protein. A HP fusion protein comprises at least a portion of a mucin protein. "At least a portion" is meant that the mucin polypeptide contains at least one mucin domain (e.g., an O-linked glycosylation site). The mucin protein comprises the extracellular portion of the polypeptide. For example, the mucin polypeptide comprises the extracellular portion of PSGL-1.

The alpha globulin polypeptide can corresponds to all or a portion of a alpha globulin polypeptide. A HP fusion protein comprises at least a portion of a alpha globulin polypeptide "At least a portion" is meant that the alpha globulin polypeptide contains at least one N-linked glycosylation site.

The first polypeptide is glycosylated by one or more blood group transferases. The first polypeptide is glycosylated by 2, 3, 5 or more blood group transferases. Glycosylation is sequential or consecutive. Alternatively glycosylation is concurrent or random, i.e., in no particular order. For example the first polypeptide is glycosylated by an α1,¾ fucosyltransferase (FUT3), an α1,2 fucosyltransferase (FUT2) and a β1,3 galactosyltransferase. Optionally, first polypeptide is further glycosylated by a β 1,3, N-acetylglucosaminyltransferase to add O-linked glycans.

Suitable sources for α1,¾ fucosyltransferase polypeptides and nucleic acids encoding α1,¾ fucosyltransferase polypeptides include GenBank Accession Nos. NP_000140 and NM_000149, BAA13941 and D89324, BAA13942 and D89325 respectively, and are incorporated herein by reference in their entirety.

Suitable sources for α1,2 fucosyltransferase polypeptides and nucleic acids encoding α1,2 fucosyltransferase polypeptides include GenBank Accession Nos. NP_000502 and NM_000511 respectively, and are incorporated herein by reference in their entirety.

Suitable sources for β1,3 galactosyltransferase polypeptides and nucleic acids encoding β1,3 galactosyltransferase polypeptides include GenBank Accession Nos. NP_058584 and NM_016888 respectively, and are incorporated herein by reference in their entirety.

Suitable sources for β 1,3, N-acetylglucosaminyltransferase polypeptides and nucleic acids encoding β 1,3, N-acetylglucosaminyltransferase polypeptides include GenBank Accession NP_653278 and NM_144677, NP_945193 and NM_198955 respectively, and are incorporated herein by reference in their entirety.

The first polypeptide is more heavily glycosylated than the native (i.e. wild-type) polypeptide. The first polypeptide contains greater that 40%, 50%, 60%, 70%, 80%, 90% or 95% of its mass due to carbohydrate Within the fusion protein, the term "operatively linked" is intended to indicate that the first and second polypeptides are chemically linked (most typically via a covalent bond such as a peptide bond) in a manner that allows for O-linked and/or N-linked glycosylation of the first polypeptide. When used to refer to nucleic acids encoding a fusion polypeptide, the term operatively linked means that a nucleic acid encoding the mucin or alpha globulin polypeptide and the non-mucin polypeptide are fused in-frame to each other. The non-mucin polypeptide can be fused to the N-terminus or C-terminus of the mucin or alpha globulin polypeptide.

The HP fusion protein is linked to one or more additional moieties. For example, the HP fusion protein may additionally be linked to a GST fusion protein in which the HP fusion protein sequences are fused to the C-terminus of the GST (i.e., glutathione S-transferase) sequences. Such fusion proteins can facilitate the purification of the HP fusion protein. Alternatively, the HP fusion protein may additionally be linked to a solid support. Various solid support are know to those skilled in the art. Such compositions can facilitate removal of anti-blood group antibodies. For example, the HP fusion protein is linked to a particle made of, e.g., metal compounds, silica, latex, polymeric material; a microtiter plate; nitrocellulose, or nylon or a combination thereof. The HP fusion proteins linked to a solid support are used as an absorber to remove microbes or bacterial toxins from biological sample, such as gastric tissue, blood or plasma.

The fusion protein is includes a heterologous signal sequence (i.e., a polypeptide sequence that is not present in a polypeptide encoded by a mucin or a globulin nucleic acid) at its N-terminus. For example, the native mucin or alpha-glycoprotein signal sequence can be removed and replaced with a signal sequence from another protein. In certain host cells (e.g., mammalian host cells), expression and/or secretion of polypeptide can be increased through use of a heterologous signal sequence.

An chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene is synthesized by conventional techniques including automated DNA synthesizers. Alternatively, PCR amplification of gene fragments is carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A mucin or a alpha-globulin encoding nucleic acid can be cloned into such an expression vector such that the fusion moiety is linked in-frame to the immunoglobulin protein.

HP fusion polypeptides may exist as oligomers, such as dimers, trimers or pentamers. Preferably, the HP fusion polypeptide is a dimer.

The first polypeptide, and/or nucleic acids encoding the first polypeptide, is constructed using mucin or alpha-globulin encoding sequences are known in the art. Suitable sources for mucin polypeptides and nucleic acids encoding mucin polypeptides include GenBank Accession Nos. NP663625 and NM145650, CAD10625 and AJ417815, XP140694 and XM140694, XP006867 and XM006867 and NP00331777 and NM009151 respectively, and are incorporated herein by reference in their entirety. Suitable sources for alpha-globulin polypeptides and nucleic acids encoding alpha-globulin polypeptides include GenBank Accession Nos. AAH26238 and BC026238; NP000598; and BC012725, AAH12725 and BC012725, and NP44570 and NM053288 respectively, and are incorporated herein by reference in their entirety.

The mucin polypeptide moiety is provided as a variant mucin polypeptide having a mutation in the naturally-occurring mucin sequence (wild type) that results in increased carbohydrate content (relative to the non-mutated sequence). For example, the variant mucin polypeptide comprised additional O-linked glycosylation sites compared to the wild-type mucin. Alternatively, the variant mucin polypeptide comprises an amino acid sequence mutations that results in an increased number of serine, threonine or proline residues as compared to a wild type mucin polypeptide. This increased carbohydrate content can be assessed by determining the protein to carbohydrate ratio of the mucin by methods know to those skilled in the art.

Similarly, the alpha-globulin polypeptide moiety is provided as a variant alpha-globulin polypeptide having a mutation in the naturally-occurring alpha-globulin sequence (wild type) that results in increased carbohydrate content (relative to the non-mutated sequence). For example, the variant alpha-globulin polypeptide comprised additional N-linked glycosylation sites compared to the wild-type alpha-globulin.

Alternatively, the mucin or alpha-globulin polypeptide moiety is provided as a variant mucin or alpha-globulin polypeptide having mutations in the naturally-occurring mucin or alpha-globulin sequence (wild type) that results in a mucin or alpha-globulin sequence more resistant to proteolysis (relative to the non-mutated sequence).

The first polypeptide includes full-length PSGL-1. Alternatively, the first polypeptide comprise less than full-length PSGL-1 polypeptide such as the extracellular portion of PSGL-1. For example the first polypeptide less than 400 amino acids in length, e.g., less than or equal to 300, 250, 150, 100, 50, or 25 amino acids in length.

The first polypeptide includes full-length alpha acid-globulin. Alternatively, the first polypeptide comprise less than full-length alpha acid globulin polypeptides. For example the first polypeptide less than 200 amino acids in length, e.g., less than or equal to 150, 100, 50, or 25 amino acids in length.

The second polypeptide is preferably soluble. In some embodiments, the second polypeptide includes a sequence that facilitates association of the HP fusion polypeptide with a second mucin or alpha globulin polypeptide. The second polypeptide includes at least a region of an immunoglobulin polypeptide. "At least a region" is meant to include any portion of an immunoglobulin molecule, such as the light chain, heavy chain, FC region, Fab region, Fv region or any fragment thereof. Immunoglobulin fusion polypeptide are known in the art and are described in e.g., U.S. Pat. Nos. 5,516,964; 5,225,538; 5,428,130; 5,514,582; 5,714,147; and 5,455,165.

The second polypeptide comprises a full-length immunoglobulin polypeptide. Alternatively, the second polypeptide comprise less than full-length immunoglobulin polypeptide, e.g., a heavy chain, light chain, Fab, $Fab_2$, Fv, or Fc. Preferably, the second polypeptide includes the heavy chain of an immunoglobulin polypeptide. More preferably the second polypeptide includes the Fc region of an immunoglobulin polypeptide.

The second polypeptide has less effector function that the effector function of a Fc region of a wild-type immunoglobulin heavy chain. Alternatively, the second polypeptide has similar or greater effector function of a Fc region of a wild-type immunoglobulin heavy chain. An Fc effector function includes for example, Fc receptor binding, complement fixation and T cell depleting activity. (see for example, U.S. Pat. No. 6,136,310) Methods of assaying T cell depleting activity, Fc effector function, and antibody stability are known in the art. In one embodiment the second polypeptide has low or no affinity for the Fc receptor. Alternatively, the second polypeptide has low or no affinity for complement protein C1q.

Another aspect of the invention pertains to vectors, preferably expression vectors, containing a nucleic acid encoding mucin polypeptides, or derivatives, fragments, analogs or homologs thereof. The vector contains nucleic acid encoding a mucin or alpha globulin polypeptide operably linked to an nucleic acid encoding an immunoglobulin polypeptide, or derivatives, fragments analogs or homologs thereof. Additionally, the vector comprises a nucleic acid encoding a blood group transferase such as a α1,3 fucosyltransferase. The blood group transferase facilitates the addition of sialyl Lewis determinants on the peptide backbone of the mucin or alpha-globulin portion of the HP fusion protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., HP fusion polypeptides, mutant forms of HP fusion polypeptides, etc.).

The recombinant expression vectors of the invention can be designed for expression of HP fusion polypeptides in prokaryotic or eukaryotic cells. For example, HP fusion polypeptides can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

The HP fusion polypeptide expression vector is a yeast expression vector. Examples of vectors for expression in yeast *Saccharomyces cerivisae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, HP fusion polypeptide can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

A nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, HP fusion polypeptides can be expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) HP fusion polypeptides. Accordingly, the invention further provides methods for producing HP fusion polypeptides using the host cells of the invention. In one embodiment, the method comprises culturing the host cell of invention (into which a recombinant expression vector encoding HP fusion polypeptides has been introduced) in a suitable medium such that HP fusion polypeptides is produced. In another embodiment, the method further comprises isolating HP polypeptide from the medium or the host cell.

The HP fusion polypeptides may be isolated and purified in accordance with conventional conditions, such as extraction, precipitation, chromatography, affinity chromatography, electrophoresis or the like. For example, the immunoglobulin fusion proteins may be purified by passing a solution through a column which contains immobilized protein A or protein G which selectively binds the Fc portion of the fusion protein. See, for example, Reis, K. J., et al., J. Immunol. 132:3098-3102 (1984); PCT Application, Publication No. WO87/00329. The fusion polypeptide may the be eluted by treatment with a chaotropic salt or by elution with aqueous acetic acid (1 M).

Alternatively, an HP fusion polypeptides according to the invention can be chemically synthesized using methods known in the art. Chemical synthesis of polypeptides is described in, e.g., A variety of protein synthesis methods are common in the art, including synthesis using a peptide synthesizer. See, e.g., *Peptide Chemistry, A Practical Textbook*, Bodasnsky, Ed. Springer-Verlag, 1988; Merrifield, *Science* 232: 241-247 (1986); Barany, et al, *Intl. J. Peptide Protein Res.* 30: 705-739 (1987); Kent, *Ann. Rev. Biochem.* 57:957-989 (1988), and Kaiser, et al, *Science* 243: 187-198 (1989). The polypeptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of polypeptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. *J. Med. Chem.* 36: 2585-2594; Kirby, et al., 1993. *J. Med. Chem.* 36:3802-3808; Morita, et al., 1994. *FEBS Lett.* 353: 84-88; Wang, et al.; 1993. *Int. J. Pept. Protein Res.* 42: 392-399; Fauchere and Thiunieau, 1992. *Adv. Drug Res.* 23: 127-159.

Introduction of covalent cross-links into a peptide sequence can conformationally and topographically constrain the polypeptide backbone. This strategy can be used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137: 5182-5185 (1996)), or between two amino acid side chains. See, e.g., DeGrado, *Adv Protein Chem*, 39: 51-124 (1988). Disulfide bridges are also introduced into linear sequences to reduce their flexibility. See, e.g., Rose, et al., *Adv Protein Chem*, 37: 1-109 (1985); Mosberg et al., *Biochem Biophys Res Commun*, 106: 505-512 (1982). Furthermore, the replacement of cysteine residues with penicillamine (Pen, 3-mercapto-(D) valine) has been used to increase the selectivity of some opioid-receptor interactions. Lipkowski and Carr, *Peptides: Synthesis, Structures, and Applications*, Gutte, ed., Academic Press pp. 287-320 (1995).

Methods of Decreasing Bacterial Adhesion

Bacterial or bacterial toxin adhesion to a cell is inhibited (e.g. decreased) by contacting a tissue or cell with the HP fusion peptide of the invention. Alternatively, adhesion is inhibited by introducing to a cell a nucleic acid encoding the HP fusion peptide. The microbe is for example a bacteria, a virus or fungus. The bacteria is for example, *Helicobacter pylori*. Tissues to be treated include an intestinal tissue, a cardiac tissue, a pulmonary tissue, a dermal tissue, or a hepatic tissue. For example, the tissue is gastric mucosal tissue. Cells include for example, gastric cells, cardiac cells, or pulmonary cells.

Inhibition of adhesion is characterized by a decrease in bacterial colonization of the affected tissue. Tissues or cells are directly contacted with the HP peptide. Alternatively, the inhibitor is administered to a subject systemically. HP peptides are administered in an amount sufficient to decrease (e.g., inhibit) bacterial adhesion. Adhesion is measured using standard adhesion assays known in the art.

The methods are useful to alleviate the symptoms of a variety of microbial infections or a disease associated with a microbial infection. The microbial infection is for example a bacterial, viral or fungal infection. The bacterial infection is for example, a *Helicobacter pylori* infection. Diseases associated with a microbial infection, e.g., *Helicobacter pylori* infection include for example, peptic acid diseases such as gastric and duodenal ulcers, gastric atrophy, gastric MALT lymphoma, and gastric adenocarcinoma.

The methods described herein lead to a reduction in the severity or the alleviation of one or more symptoms of an microbial infection or disorder such as those described herein. Microbial infection or disorders associated with a microbial infection are diagnosed and or monitored, typically by a physician using standard methodologies Symptoms of *Helicobacter pylori* infection and disorders associated *Helicobacter pylori* infection with include for example, abdominal discomfort, weight loss, poor appetite, bloating, burping, nausea or vomiting. *Helicobacter pylori* infection is diagnosed using blood, breath, stool and tissue test. Ulcers are diagnosed for example, an upper GI series or endoscopy. Gastric MALT lymphoma and gastric adenocarcinoma ae diagnosed for example histopathogically by biopsy.

The subject is e.g., any mammal, e.g., a human, a primate, mouse, rat, dog, cat, cow, horse, pig. The treatment is administered prior to microbial infection or diagnosis of the disorder. Alternatively, treatment is administered after a subject has an infection.

Efficaciousness of treatment is determined in association with any known method for diagnosing or treating the particular bacterial infection or disorder associated with a microbial infection. Alleviation of one or more symptoms of the bacterial infection or disorder indicates that the compound confers a clinical benefit.

Pharmaceutical Compositions Including HP Fusion Polypeptides or Nucleic Acids Encoding Same The HP fusion proteins, or nucleic acid molecules encoding these fusion proteins, (also referred to herein as "Therapeutics" or "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an HP fusion protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Leb Expressing Cells

The invention provides a genetically modified Leb expressing cell (referred to herein as LBC).

The term "genetic modification" refers to the stable or transient alteration of the genotype of a LBCs by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

The cells are genetically modified with a nucleic acid encoding a β 1,3, N-acetylglucosaminyltransferase gene (βGn-T6) a β1,3 galactosyltransferase (β3Gal-T5) gene, a α1,¾ fucosyltransferase gene (Fuc-T3) and a α1,2 fucosyltransferase gene (FucT-2). Suitable sources or the nucleic acid sequences encoding theses genes are well know in the art and include those sequences described herein.

The genetic modification is performed either by infection with viral vectors (retrovirus, modified herpes viral, herpesviral, adenovirus, adeno-associated virus, and the like) or transfection using methods known in the art (lipofection, calcium phosphate transfection, DEAE-dextran, electroporation, and the like) (see, Maniatis et al., in *Molecular Cloning: A Laboratory Manual* (Cold Spring Harbor Laboratory, N.Y., 1982)). For example, the chimeric gene constructs can contain viral, for example retroviral long terminal repeat (LTR), simian virus 40 (SV40), cytomegalovirus (CMV); or mammalian cell-specific promoters such as tyrosine hydroxylase (TH, a marker for dopamine cells), DBH, phenylethanolamine N-methyltransferase (PNMT), ChAT, GFAP, NSE, the NF proteins (NE-L, NF-M, NF-H, and the like) that direct the expression of the structural genes encoding the desired protein. In addition, the vectors can include a drug selection marker, such as the *E. coli* aminoglycoside phosphotransferase gene, which when co-infected with the test gene confers resistance to geneticin (G418), a protein synthesis inhibitor.

LBCs can be genetically modified using transfection with expression vectors. In one protocol, vector DNA containing the genes are diluted in 0.1× TE (1 mM Tris pH 8.0, 0.1 mM EDTA) to a concentration of 40 μg/ml. 22 μl of the DNA is added to 250 μl of 2× HBS (280 mM NaCl, 10 mM KCl, 1.5 mM $Na_2HPO_4$, 12 mM dextrose, 50 mM HEPES) in a disposable, sterile 5 ml plastic tube. 31 μl of 2 M $CaCl_2$ is added slowly and the mixture is incubated for 30 minutes (min) at room temperature. During this 30 min incubation, the cells are centrifuged at 800 g for 5 min at 4° C. The cells are resuspended in 20 volumes of ice-cold PBS and divided into aliquots of $1×10^7$ cells, which are again centrifuged. Each aliquot of cells is resuspended in 1 ml of the DNA-$CaCl_2$ suspension, and incubated for 20 min at room temperature. The cells are then diluted in growth medium and incubated for 6-24 hr at 37° C, in 5%-7% $CO_2$. The cells are again centrifuged, washed in PBS and returned to 10 ml of growth medium for 48 hr.

LBCs are also genetically modified using calcium phosphate transfection techniques. For standard calcium phosphate transfection, the cells are mechanically dissociated into a single cell suspension and plated on tissue culture-treated dishes at 50% confluence (50,000-75,000 cells/$cm^2$) and allowed to attach overnight. In one protocol, the modified calcium phosphate transfection procedure is performed as follows: DNA (15-25 μg) in sterile TE buffer (10 mM Tris, 0.25 mM EDTA, pH 7.5) diluted to 440 μL with TE, and 60 μL of 2 M $CaCl^2$ (pH to 5.8 with 1M HEPES buffer) is added to the DNA/TE buffer. A total of 500 μL of 2× HeBS (HEPES-Buffered saline; 275 mM NaCl, 10 mM KCl, 1.4 mM $Na_2$ $HPO_4$, 12 mM dextrose, 40 mM HEPES buffer powder, pH 6.92) is added dropwise to this mix. The mixture is allowed to stand at room temperature for 20 min. The cells are washed briefly with 1× HeBS and 1 ml of the calcium phosphate precipitated DNA solution is added to each plate, and the cells are incubated at 37° C. for 20 min. Following this incubation, 10 ml of medium is added to the cells, and the plates are placed in an incubator (37° C., 9.5% $CO_2$) for an additional 3-6 hours. The DNA and the medium are removed by aspiration at the end of the incubation period, and the cells are washed 3 times and then returned to the incubator.

The LBC is capable of self-maintenance, such that with each cell division, at least one daughter cell will also be a LBC cell. LBC are capable of being expanded 100, 250, 500, 1000, 2000, 3000, 4000, 5000 or more fold.

Exemplary LBCs include the 1C5 and 2C2. Phenotyping the LBCs revele that 1C5, expresses $Le^b$ on O-glycans, but not on N-glycans or glycolipids. In contrast, 2C2, expresses $Le^b$ on O- and N-glycans as well as on glycolipids. Furthermore, 1C5 does not express $Le^y$, whereas 2C2 does. Despite these differences in glycan repertoire, difference between these clones in terms of *H. pylori* adherence was detected LBCs can be maintained in vitro in long-term cultures. The LBCs are capable of being passed in culture 2, 3, 4, 5, 6, 7, 8, 9, 10, 11, 12 or more times.

LBCs are proliferated using methods well known in the art. Conditions for culturing should be close to physiological conditions. The pH of the culture medium should be close to physiological pH. (for example, between pH 6-8, between about pH 7 to 7.8, or at pH 7.4). Physiological temperatures range between about 30° C. to 40° C. LBCs are cultured at temperatures between about 32° C. to about 38° C. (for example, between about 35° C. to about 37° C.).

Generally, after about 3-10 days in vitro, the proliferating LBCs by aspirating the medium, and adding fresh medium to the culture flask. Optionally, the aspirated medium is collected, filtered and used as a condition medium to subsequently passage LBCs. For example the 10%, 20%, 30%, 40% or more condition medium is used.

The LBC cell culture can be easily passaged to reinitiate proliferation. For example after 3-7 days in vitro, the culture flasks are shaken well and LBCs are then transferred to a 50 ml centrifuge tube and centrifuged at low speed. he medium is aspirated, the LBCs are resuspended in a small amount of culture medium The cells are then counted and replated at the desired density to reinitiate proliferation. This procedure can be repeated weekly to result in a logarithmic increase in the number of viable cells at each passage. The procedure is continued until the desired number of LBCs is obtained.

LBCs and LBC progeny can be cryopreserved by any method known in the art until they are needed. (See, e.g., U.S. Pat. No. 5,071,741, PCT International patent applications WO93/14191, WO95/07611, WO96/27287, WO96/29862, and WO98/14058, Karlsson et al., 65 Biophysical J. 2524-2536 (1993)). The LBCs can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15% (for example, 8-10%). Cells are frozen gradually to a temperature of −10° C. to −150° C. (for example, −20° C. to −100° C., or −70° C. to −80° C.).

Methods for Screening Effects of Drugs on $Le^b$ Expressing Cells

LBCs cultures can be used for the screening of potential therapeutic compositions. For example LBCs are used to identify compounds that mediate, e.g. enhance or inhibit *H. pylori* adhesion or bind Leb carbohydrate epitope. These test compositions can be applied to cells in culture at varying dosages, and the response of the cells monitored for various time periods. Physical characteristics of the cells can be analyzed by observing cell growth and morphology with microscopy.

In various methods, an inhibitor or enhancer of the *H. pylori* interaction is identified by contacting a LBC with a *H. pylori* bacterium and a test compound under conditions where LBC and *H. pylori* bacterium are capable of forming a complex and the amount of complex formation is determined. A decrease in the amount of complex formation in the presence of the test compound compared to the absence of the test compound indicates that the test compound in as inhibitor of *H. pylori* adhesion. In contrast, an increase in the amount of complex formation in the presence of the test compound compared to the absence of the test compound indicates that the test compound in as enhancer of *H. pylori* adhesion.

The invention also provide a method of identifying an agent that binds a $Le^b$ carbohydrate epitope by contacting a LBC with a $Le^b$ epitope binding agent, e.g., *H. pylori* bacterium with a test agent and determining whether the agent binds the LBC, e.g. forms a complex. A decrease in the amount of complex formation in the presence of the test compound compared to the absence of the test compound indicates that the test compound binds a $Le^b$ carbohydrate epitope.

The invention also includes an modulator compounds identified according to these screening methods, and a pharmaceutical composition which includes the modulators.

The invention will be further illustrated in the following non-limiting examples.

EXAMPLE 1

General Methods

Antibodies

The mouse anti-$Le^b$ (IgM, clone T218) antibodiy was purchased from Signet (Dedham, Mass., USA), the mouse anti-sialyl-$Le^x$ antibody (IgM, clone KM93) was purchased from Calbiochem-Novabiochem (San Diego, Calif., USA), and the CSLEX (IgM) antibody was produced by the CSLEX mouse hybridoma cell line (ATCC, Manassas, Va., U.S.A.). The HRP-conjugated goat anti-mouse IgM antibody was purchased from Cappel (Durham, N.C., USA).

All immunohistochemical staining experiments for FACS were performed in 1% bovine serum albumin (BSA; Sigma) in phosphate buffered saline (PBS). Alexa 488 conjugated (Molecular Probes) goat anti-mouse IgM and IgG was used as secondary antibodies at a dilution of 1:2,000-4,000. Anti-$Le^a$ (T174, $IgG_1$; Calbiochem) was used in a dilution of 1:50-100. Anti-$Le^a$ (78FR2.3; IgM; Biomed) was used in a dilution of 1:200

Anti-$Le^b$ (BG-6, IgM; Signet) was used in a dilution of 1:200. Anti-$Le^y$ (F3, IgM; Calbiochem) was used in a dilution of 1:200.

*H. pylori* Strains and Culture

The $Le^b$ and $SLe^x$-binding *Helicobacter pylori* strain Cag7.8 was grown on *Brucella* agar supplemented with 10% bovine blood and 1% IsoVitalex for two days in a microaerophilic atmosphere at 37° C. (BBL GasPak Plus, Becton Dickinson and Company, Sparks, Md. 2152).

The *H. pylori* strain 17875/$Le^b$ was used (18). *H. pylori* was cultured for 48-72 hours on blood agar plates, supplemented with 2% FCS and isovitalex. Bacteria were transferred to a 1.5 ml eppendorf tube using a sterile inoculation loop (Sarstedt) and PBS. The cells were spun down at 5,000 rpm, supernatant was removed and the bacteria were resuspended in 1 ml of PBS. $OD_{600}$ was adjusted to 0.1.

The bacteria were FITC-labelled and cells overlayed with them as described before (19).

Cell Culture

CHO-K1 cells and stable transfectants thereof were cultured in DMEM (Gibco) supplemented with 10% heat inactivated fetal bovine serum (FBS; Gibco) and glutamine (Gibco), as previously described (15).

Transfection of CHO-K1 Cells

Adherent CHO-K1 cells were seeded in 75 cm$^2$ T-flasks and were transfected approximately 24 hours later at a cell confluency of 70-80%. Transient transfections were accomplished by a modified polyethylenimine (PEI) transfection method or by lipofectamine as described by the manufacturer (Invitrogen).

In all transfection mixtures, 19.5 μg of fusion protein plasmid was used. Because of low transfection efficiency, CHO-K1 cells were transfected with lipofectamine 2000 as recommended by the manufacturer. For stable transfectants, plasmids were linearized with AvrII or Spe1, and subsequently transfected into CHO-K1 cells, using lipofectamine 2000 according to the manufacturer (Invitrogen). Twenty-four hours after transfection, cells in each T-flask were split into five 100 mm petri dishes and incubated in selection medium. The concentrations of the different selection drugs were 400 μg/ml, 200 μg/ml, and 0.5 mg/ml for zeocin, hygromycin B, and G418, respectively. Gpt expressing cells were selected by growth in medium containing mycophenolic acid (25 μg/ml), xanthine (13.6 μg/ml) and hypoxanthine (0.25 mg/ml). The selection medium was changed every third day. The drug resistant clones formed after approximately two weeks. Clones were identified under the microscope and handpicked using a pipetman. Selected colonies were cultured in 96-well plates in the presence of selection drugs for another two weeks.

One-Dimensional SDS-PAGE and Western Blotting

SDS-PAGE was run on 4-12% Bis-Tris discontinuous polyacrylamide gels (NuPAGE; Invitrogen, Calif., U.S.A) using a MES-buffert and non-reducing conditions. Separated proteins were electrophoretically blotted onto nitrocellulose membranes (Invitrogen) using a Mini Trans-Blot electrophoretic transfer cell (Bio-Rad, Hercules, Calif.). Membranes were blocked overnight in phosphate-buffered saline with 0.2% Tween-20 (PBS-T) and 3% BSA, and were then incubated in room temperature for 1 hour with the anti-Le$^b$ antibody diluted in blocking buffer. Membranes were washed with PBS-T five times and incubated with the HRP-conjugated secondary antibody. Bound antibodies were detected using the ECL Western blotting reagents (Amersham Biosciences) followed by exposure of the membrane on Hyperfilm ECL (Amersham Biosciences).

Recombinant fusion proteins were purified by immunoprecipitation as done before (15). In brief, 10 ml of supernatant from transfected cells was incubated overnight at 4° C. with 100 μl of goat anti-mouse IgG-agarose beads in slurry (Sigma). The beads were spun down for 15 min at approximately 200 g, supernatant was discarded and the beads were transferred to 1.5 ml eppendorf tubes, and washed twice in PBS. Beads were mixed with 100 μl of 2× LDS-sample buffer (Invitrogen) and heated at 70° C. for 10 minutes. Samples, typically 10 μl, were loaded on a 4-12% NUPAGE-gel (Invitrogen). Electrophoresis was done at 200V, for about 60 min. For Western blotting, the samples were blotted onto 0.2 μm nitrocellulose membranes (Invitrogen) at 40V for 2 hours. Membranes were blocked with 3% BSA/PBS with 0.05% Tween 20 (PBST) overnight at 4° C. or at room temperature for an hour. An one-hour incubation with primary antibody followed by three washes and one-hour incubation with secondary antibody, repeated by three washes, were performed. Thereafter, membranes were developed using ECL plus (Amersham) following the manufacturer's instructions.

Goat anti-mouse IgM HRP (Pierce) was used at a dilution of 1:80,000 to 1:160,000. Western blots were performed in 3% BSA/PBST.

H. pylori Adhesion Assay

Bacterial grade Petri dishes were coated at 4° C. over night with 50 μl of a goat anti-mouse IgG Fc-specific antibody at a concentration of 20 μg/ml in PBS. After the incubation, the dishes were washed 3 times in PBS, which was aspirated completely after the last wash. Hereafter, 100 μl of crude supernatant from stably (SLe$^x$-carrying PSGL-1/mIgG$_{2b}$ was from 293T cells) or transiently (the Le$^b$ and Le$^a$-carrying PSGL-1/mIgG$_{2b}$ were from CHO-K1) transfected cell lines were added to each dot. Control PSGL-1/mIgG$_{2b}$ was produced in the insect cell line, Hi-5. Dishes were incubated for three hours at room temperature, and were then washed three times with PBS. A 100 μl of H. pylori suspension (~1×10$^8$ bacteria/ml) were added to each dot. Dishes were incubated on ice for 30 minutes, followed by washing twice with PBS. Bacteria that had adhered were fixed by formaldehyde in PBS and were analysed by inverted phase contrast microscopy.

FACS Analysis

A FACSort flow cytometer (BectonDickinson) was used and 10 000 events were collected. Cells were prepared for analysis in the following manner: cells were first washed twice with PBS. They were then incubated with 1% EDTA until they were detached. Cells were suspended in PBS and spun down at 200 g for 5 min. Supernatant was removed and the cells were resuspended in PBS and spun down once more. Primary antibody was added and the staining was performed at 4° C. for 30 min. Two wash steps in PBS were done and staining with secondary antibody was done as for primary antibody. Subsequently, the cells were washed twice in PBS and kept at 4° C. until FACS analysis. Negative control staining was performed with only secondary antibodies.

Construction of Vectors

Fusion proteins. The expression plasmid encoding the P-selectin glycoprotein ligand-1 mouse IgG$_{2b}$ fusion protein was constructed as described before (ref). The α1-acid glycoprotein (AGP)-coding sequence was PCR amplified, excluding the stop codon and the leader peptide (Table I), from a human liver cDNA library. The AGP cDNA was fused in frame with the cDNA encoding the CD5 leader sequence upstream and the Fc portion of mouse IgG$_{2b}$ downstream using the NheI and BamHI sites in the expression cassette. The same vector backbone was used for both fusion protein constructs.

β3GlcNAc-T6. The C3 β3GlcNAc-T6 (20) was PCR amplified from human stomach cDNA using cgc ggg aag ctt acc atg gct ttt ccc tgc cgc (SEQ ID NO: 1) as forward and cgc ggg tct aga tca gga gac ccg gtg tcc (SEQ ID NO: 2) as reverse primer, and was subcloned into CDM8 using HindIII and XbaI.

β3Gal-T5. β3Gal-T5 (21) was amplified by PCR using genomic DNA from human placenta as template with cgc ggg aag ctt acc atg gct ttc ccg aag atg (SEQ ID NO: 3) as forward and cgc ggg cgg ccg ctt tag aca ggc gga caa tct tc (SEQ ID NO: 4) as reverse primer, and were subsequently subcloned into the CDM8 expression plasmid using HindIII and NotI.

α1,2Fuc-T2. The FUT-II (Secretor gene) (22) cDNA was amplified and subcloned as described (23).

α1,¾Fuc-TIII. The Lewis gene encoded α1,¾fucosyltransferase (FUT-III) (24) expression plasmid was a kind gift of Prof. Brian Seed, Dept. of Molecular Biology, MGH, Boston, Mass., USA.

The vectors used to generate stable transfectants were bidirectional having the CMV promoter upstream of a polylinker identical to the one in CDM8, a splice donor and acceptor site, and the bidirectional poly(A) addition signal of SV40; opposite in orientation to this transcription unit, and utilizing the poly(A) signals from the opposite direction was a second transcription unit consisting of the HSV TK promoter followed by the coding sequences for the guanosine phosphoribosyl transferase (CMV/Gpt), the hygromycin b (CMV/Hyg), the zeocin (CMV/Zeo) and the neomycin (CMV/Neo) resistance genes (J. Holgersson and B. Seed, unpublished). The cDNAs described above were swapped into the vector for stable expression using the restriction enzymes described above. The C3 GnT-VI, carried the zeocin resistance gene; the GalT-V plasmid, carried GPT; FUT-II, carried the neomycin resistance gene; FUT-III, the hygromycin resistance gene.

Construction of CHO Cells Stably Expressing PSGL-1/mIgG$_{2b}$ and AGP/mIgG$_{2b}$ carrying the Le$^b$ Carbohydrate Epitope Adherent CHO-K1 cells were transfected as described above using linearized expression plasmids encoding PSGL-1/mIgG$_{2b}$ or AGP/mIgG$_{2b}$, β3GlcNAcT6, β3GalT5, FUT2 and FUT3, each of which also contained a drug selection element (puromycin, zeocin, guanosine phosphoribosyl transferase, neomycin and hygromycin b, respectively). Twenty-four hours after transfection, cells in each T-flask were split into five 100 mm petri dishes and incubated in selection medium. The selection medium was changed every third day. The drug resistant clones formed after approximately two weeks. Clones were identified under the microscope and handpicked using a pipetman. Selected colonies were cultured in 96-well plates in the presence of selection drugs for another two weeks. Cell culture supernatants were harvested when the cells had reached 80-90% confluency, and the concentration of PSGL-1/mIgG$_{2b}$ and the Le$^b$ determinant was assessed by ELISA using a goat anti-mouse IgG Fc antibody or the anti-Le$^b$ antibody followed by a HRP or ALP-conjugated, secondary anti-mouse IgM antibody.

EXAMPLE 2

Expression In CHO-K1 Cells Of A Mucin-Type Fusion Protein, PSGL-1/mIgG$_{2B}$ Carrying The Le$^B$ Carbohydrate Determinant CHO-K1 cells were transiently transfected with expression plasmids encoding PSGL-1/mIgG$_{2b}$, and the glycosyltransferases β3GlcNAcT6, β3GalT5, FUT2 (the Se gene encoded α1,2 fucosyltransferase) and FUT3 (the Lewis gene encoded α1,¾ fucosyltransferase). Cell culture supernatants of transfected CHO cells were incubated with agarose beads coupled to an anti-mouse IgG antibody; beads which were subsequently washed and boiled in SDS-PAGE sample buffer. Affinity-purified proteins from transfected CHO cell supernatants were separated by SDS-PAGE, and analysed by Western blotting using monoclonal anti-Le$^b$ antibodies (FIG. 1). In lanes 1, 2 and 5, 6 strong Le$^b$-reactivity was found of immuno-affinity purified Ig-containing proteins isolated from supernatants of CHO cells transfected with all of the above mentioned cDNAs. However, when the plasmids encoding β3GalT5 (lanes 3 and 4), FUT2 (lanes 7 and 8), or both FUT2 and FUT3 (lane 9) were excluded from the transfection mix, a very weak anti-Le$^b$ reactivity was seen of an immuno-affinity purified Ig-containing protein of the expected size of monomeric PSGL-1/mIgG$_{2b}$ (FIG. 1A and B). The weak staining seen in lanes without all cDNAs is mostly likely the result of background staining caused by secondary antibody binding.

EXAMPLE 3

Construction Of Stable CHO Cell Lines Producing PSGL-1 Or AGP mIgG$_{2B}$ Fusion Proteins Carrying The Le$^B$ Carbohydrate Epitope.

Figure 2:
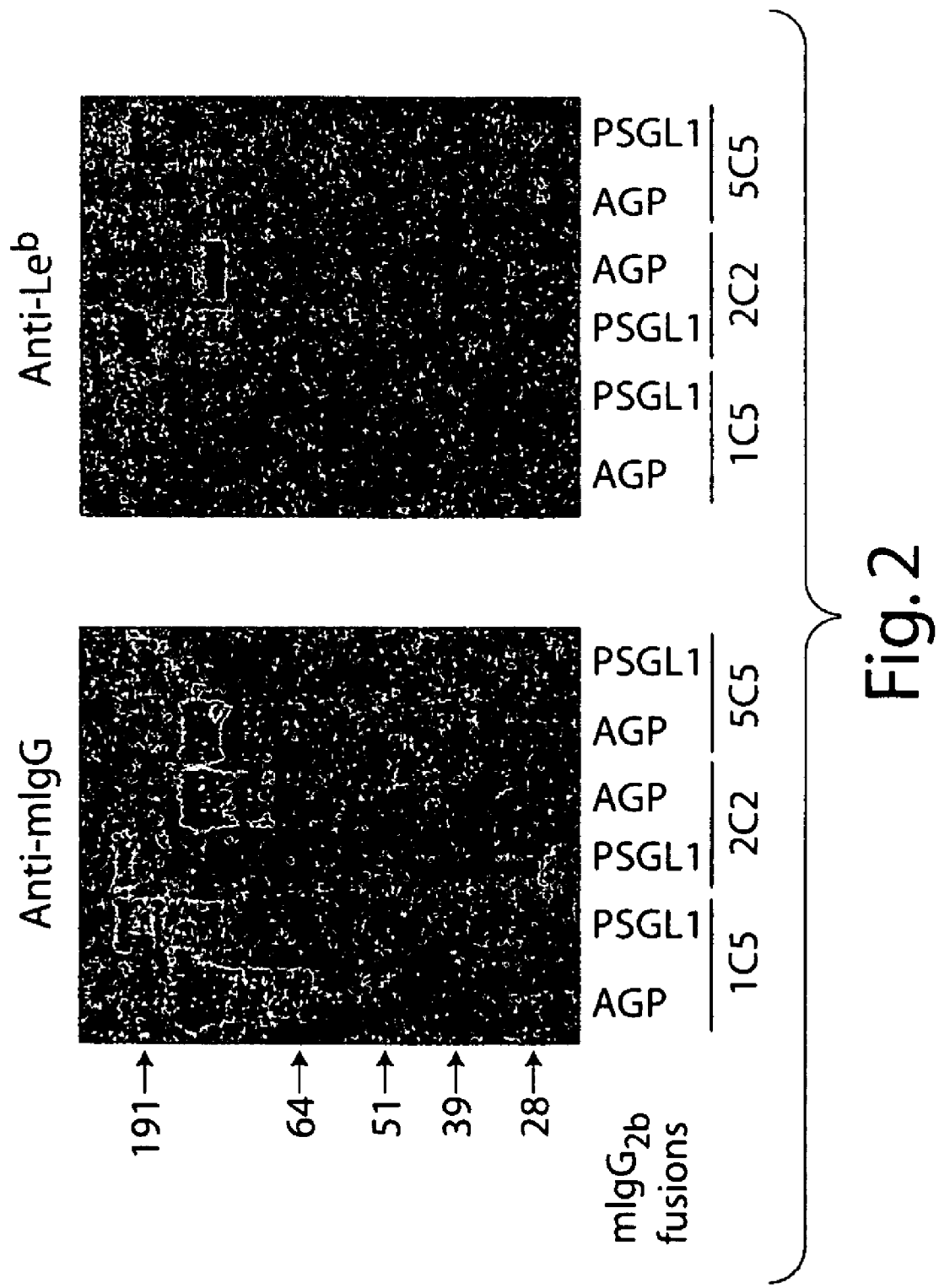
FIG. 2 is a photograph of a Western blot showing luminescence from the binding of anti-mouse IgG or monoclonal anti-Le$^b$ antibodies. The lanes contain elutions obtained from lysates incubated with agarose beads coupled to anti-mouse IgG$_{2b}$ from either 1C5, 2C2 or 5C5 strain of CHO cells transfected with expression plasmids for β3GlcNAcT6, βGalT5, FUT2, and FUT3, and which have been transiently transfected to express either P-selectin glycoprotein ligand-1 (PSGL-1) or α$_1$-acid glycoprotein (AGP).

CHO-K1 cells were simultaneously transfected with plasmids containing the glycosyltransferase cDNAs β3GlcNAcT6, β3GalT5, FUT2 and FUT3 in combination with drug resistance elements that allowed selection with a mixture of zeocin, mycophenolic acid, neomycin and hygromycin b, respectively. Several clones were handpicked using a pipetman, and three of them (FIG. 2, clones 1C5, 2C2 and 5C5) exhibited strong surface staining with anti-Le$^b$ antibodies. Following transient transfection of these clones with expression plasmids encoding the mouse IgG$_{2b}$ fusions of P-selectin glycoprotein ligand-1 (PSGL-1) or α$_1$-acid glycoprotein (AGP), the PSGL-1/mIgG$_{2b}$ and AGP/mIgG$_{2b}$ proteins were isolated from supernatants using anti-mIgG agarose beads. Western blotting revealed Le$^b$ reactivity on PSGL-1/mIgG$_{2b}$ expressed in all three clones (FIG. 2), whereas strong Le$^b$ reactivity was found only on AGP/mIgG$_{2b}$ produced in clone 2C2. AGP/mIgG$_{2b}$ produced in 1C5 appeared not to carry any Le$^b$ determinants and AGP/mIgG$_{2b}$ produced in 5C5 showed weak anti-Le$^b$ reactivity (FIG. 2). This observation indicates that CHO cells is susceptible to changes in N-glycan biosynthesis such that variants lacking the precursor chains for the above mentioned glycosyltransferases may arise during CHO culture and selection. In contrast, O-glycan biosynthesis appears more stable and less susceptible to cultivation induced changes in O-linked glycan structures. CHO stables secreting Le$^b$-carrying AGP/mIgG$_{2b}$ was constructed by stably transfecting clone 2C2 described above with a plasmid encoding AGP/Ig and puromycin acetyl transferase. CHO-K1 stables producing Le$^b$-carrying PSGL-1/mIgG$_{2b}$ were made by co-transfecting the PSGL-1/Ig expression plasmid with all of the above mentioned glycosyltransferase plasmids.

EXAMPLE 4

β3GalT1, –T2 and T5 Can All Support Le$^B$ Biosynthesis On N-glycans In The Presence Of FUT2 and FUT3

Figure 3:
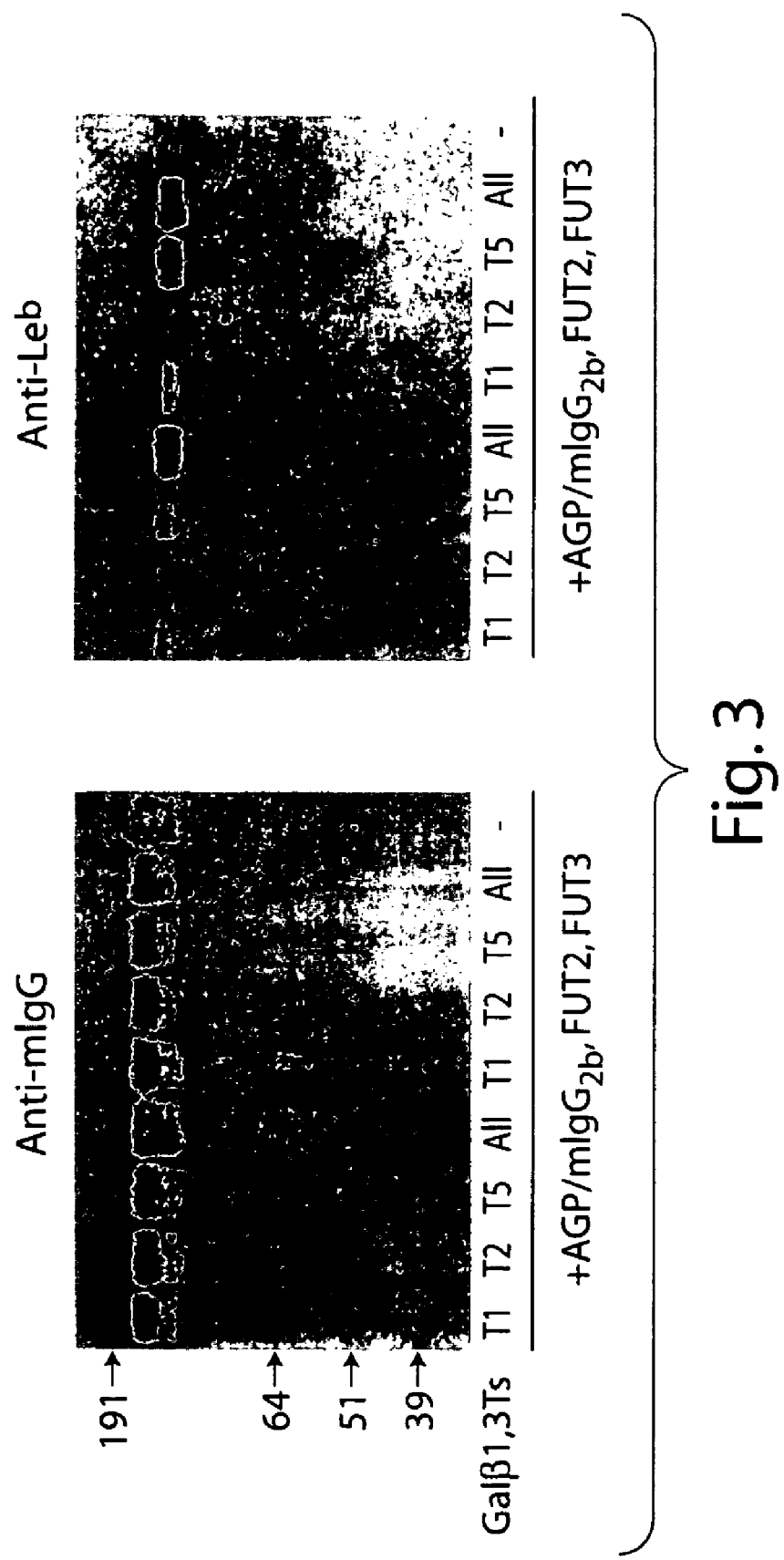
FIG. 3 is a photograph of a Western blot showing luminescence from the binding of anti-mouse IgG or monoclonal anti-Le$^b$ antibodies. The lanes contain elutions from lysate incubated with agarose beads coupled to anti-mouse IgG$_{2b}$ from CHO cells transfected with expression plasmids for α$_1$-acid glycoprotein (AGP), FUT2 and FUT3 and either βGalT1, T2, T5 or all three.
Figure 4A:
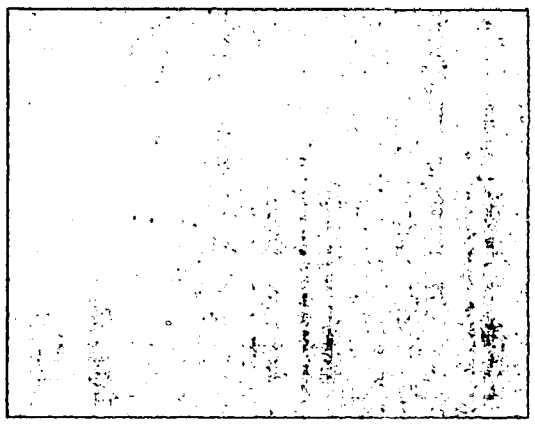
FIG. 4A is a photograph of an adhesion assay wherein mouse IgG is incubated on a dish. A lysate from insect cell line Hi-5 containing PSGL-1/mIgG2b without either Lewis epitope is spotted onto the dish so that it binds with the mouse IgG. H. pylori were then added to the dish and fixed with formaldehyde wherein their presence was discerned by inverted phase contrast microscopy.
Figure 4C:
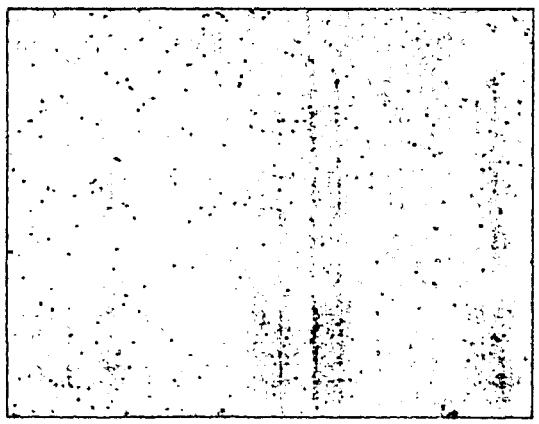
FIG. 4C is a photograph of an adhesion assay wherein mouse IgG is incubated on a dish. A lysate is spotted onto the dish so that it binds with the mouse IgG. H. pylori were then added to the dish and fixed with formaldehyde wherein their presence was discerned by inverted phase contrast microscopy.
Figure 4B:
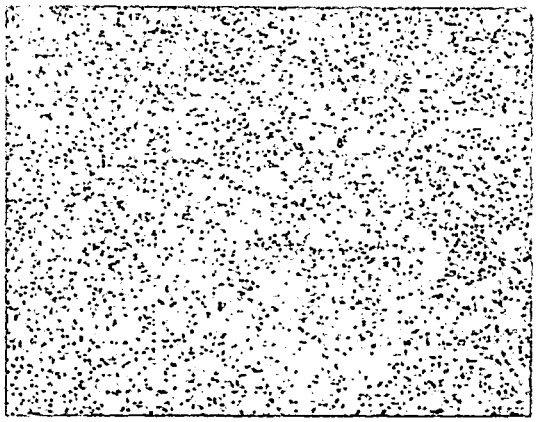
FIG. 4B is a photograph of an adhesion assay wherein mouse IgG is incubated on a dish. A lysate from 293T cells containing SLe$^x$-carrying PSGL-1/mIgG2b is spotted onto the dish so that it binds with the mouse IgG. H. pylori were then added to the dish and fixed with formaldehyde wherein their presence was discerned by inverted phase contrast microscopy.
Figure 4D:
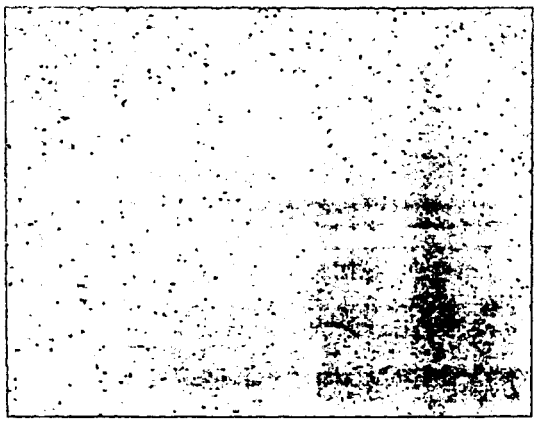
FIG. 4D is a photograph of an adhesion assay wherein mouse IgG is incubated on a dish. A lysate from CHO cells containing SLe$^b$-carrying PSGL-1/mIgG2b is spotted onto the dish so that it binds with the mouse IgG. H. pylori were then added to the dish and fixed with formaldehyde wherein their presence was discerned by inverted phase contrast microscopy.

Using AGP/mIgG$_{2b}$, a reporter protein carrying only N-linked glycans, the ability of β3GalT1, –T2 and –T5 to support Le$^b$ biosynthesis on N-linked glycans (FIG. 3) was investigated. β3GalT1, –T2 and –T5 were all capable of supporting Le$^b$ biosynthesis on AGP/Ig when FUT2 and FUT3 were co-transfected (FIG. 3). Note that the β3GlcNAcT6 transferase, which is needed for Le$^b$ biosynthesis on O-linked glycans of PSGL-1/mIgG$_{2b}$, is not required for Le$^b$ biosynthesis on N-glycans.

EXAMPLE 5

Le$^B$-and sialyl-Le$^X$-subsituted PSGL-1/mIgG$_{2b}$ Support Helicobacter Pylori Adhesion The ability of Le$^b$ and sialyl-Le$^x$-subsituted PSGL-1/mIgG$_{2b}$ to support *H. pylori* adhesion was investigated in adhesion assays. Compared to PSGL-1/mIgG$_{2b}$ carrying short core 1 structures (FIG. 4 A), $Le^b$-(FIG. 4 D) and more than that sialyl-$Le^x$- (FIG. 4 B) substituted PSGL-1/$mIgG_{2b}$ supported binding of an *H. pylori* strain known to bind $Le^b$- and sialyl-$Le^x$ carrying glycoconjugates (FIG. 4).

EXAMPLE 6

Generation Of Stable CHO-K1 Cell Lines Expressing Lewis B

Figure 5:
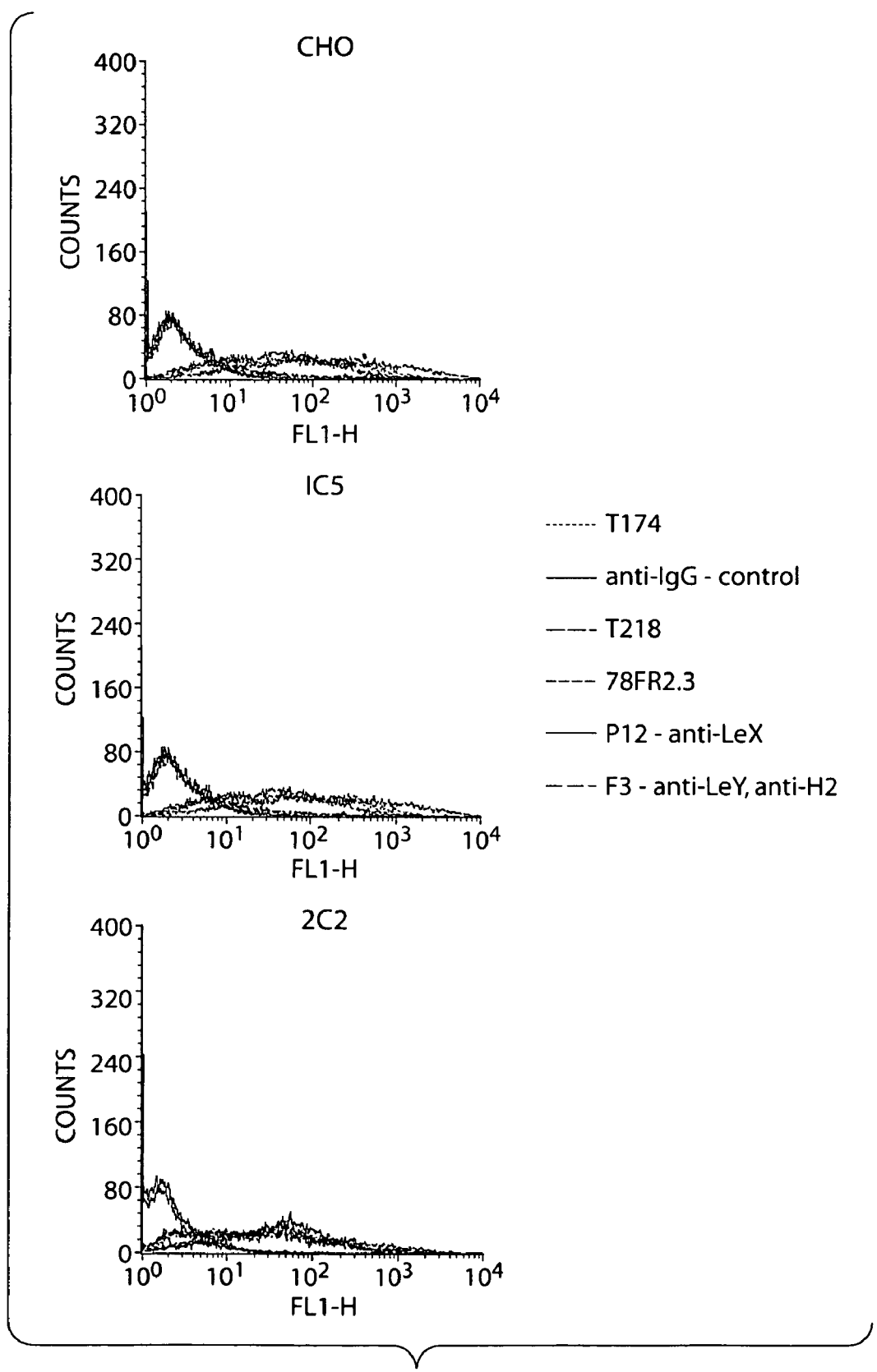
FIG. 5 is a series of charts showing flow cytometric analysis of Lewis antigen expression on CHO-K1, 1C5 and 2C2 cells. T174 and 78FR2.3 are both anti-Le$^a$ Abs; T218 is an anti-Le$^b$ Ab; P12 is an anti-Le$^x$ Ab; and F3 is an anti-Le$^y$ Ab crossreacting with H type 2 structures.

Following co-transfection of expression vectors encoding β3GlcNAc-T6, β3Gal-T5, α2Fuc-T2 and α¾Fuc-T3 a number of clones were picked using a pipetman, and transferred to 96-well plates. Following expansion the wells with growing cells were split into duplicate wells and stained with anti-$Le^b$ antibodies. Two positive clones were expanded further, 1C5 and 2C2, and were single-cell cloned using an estimated cell density of 0.3 cells per well. By flow cytometry both clones were found to express $Le^a$ and $Le^b$ epitopes, whereas only 2C2 expressed the type 2 isomer of $Le^b$ called $Le^y$ (FIG. 5). Neither of the clones expressed any detectable $Le^x$.

EXAMPLE 7

1C5 And 2C2 Express Lewis B On Different Glycans

Figure 6:
FIG. 6 are photographs showing SDS-PAGE and Western blot analysis of AGP/mIgG$_{2b}$ (A) and PSGL-1/mIgG$_{2b}$ (P) fusion proteins expressed in the Le$^b$-expressing 1C5 and 2C2 cell lines. In the left panel an anti-Le$^b$ Ab (T218) was used and in the right panel the fusion proteins were detected by an anti-mouse IgG mAb.
Figure 6:
Figure 7:
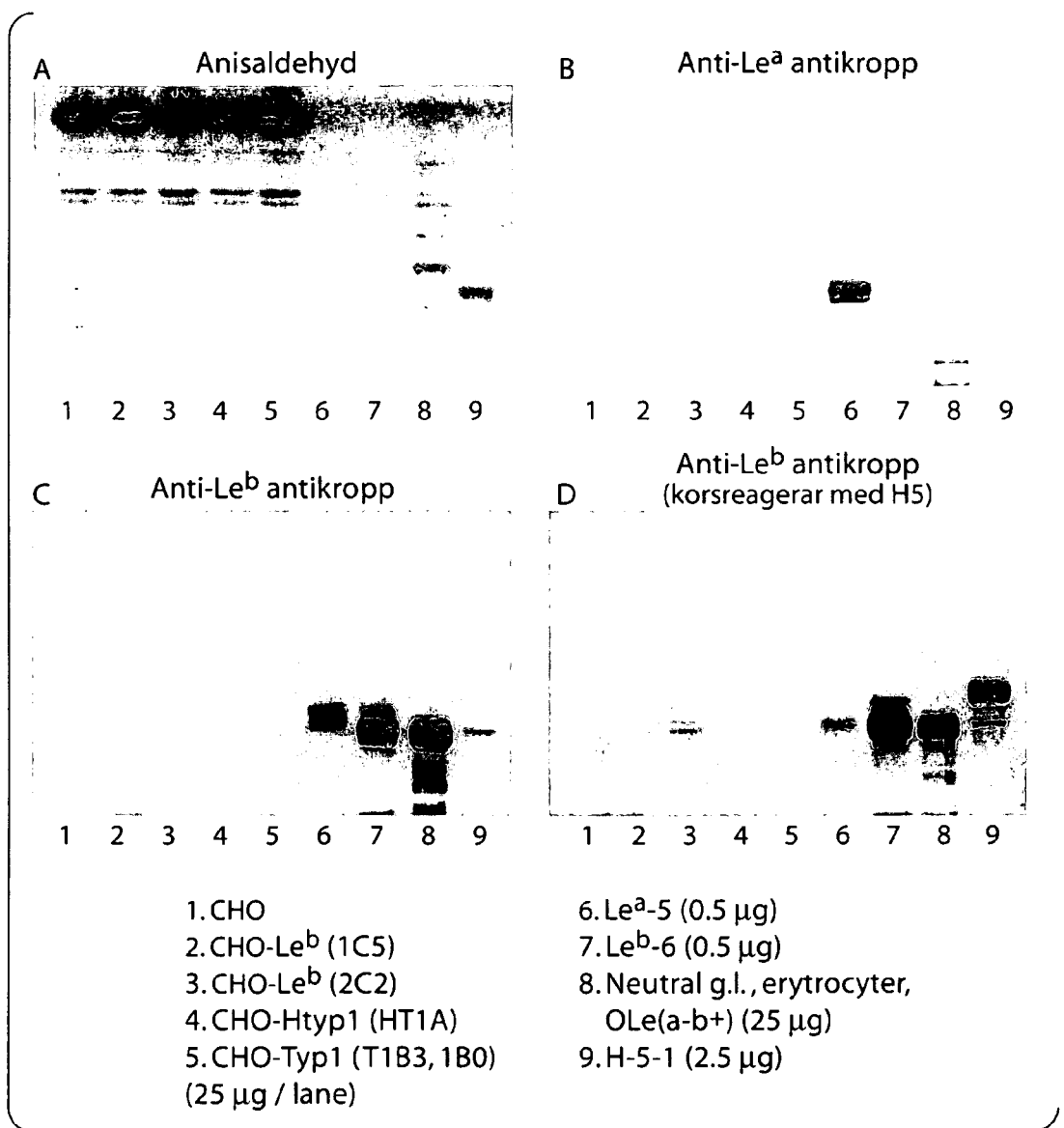
FIG. 7 are a series of photographs showing thin-layer chromatographic analysis of total non-acid glycosphingolipids isolated from CHO-K1, 1C5 and 2C2 cells. The chromatograms were either developed with a chemical reagent, anisaldehyde, staining glycosphingolipids green (panel A), or were probed with anti-Le$^a$ (panel B) or Le$^b$ (panel C and D) antibodies.

1C5 and 2C2 were transfected with plasmids encoding immunoglobulin fusion proteins of a1-acid glycoprotein (AGP) and P-selectin glycoprotein ligand-1 (PSGL-1), which are proteins carrying N-linked and O-linked glycans, respectively. Following secretion into the culture medium, AGP/$mIgG_{2b}$ and PSGL-1/$mIgG_{2b}$ were affinity purified on anti-mouse IgG agarose beads and analyzed by SDS-PAGE and Western blotting using anti-$Le^b$ and anti-mouse IgG antibodies (FIG. 6). Interestingly, fusion proteins expressed in 2C2 cells expressed $Le^b$ on both N- and O-glycans, whereas fusion proteins expressed in 1C5 cells expressed $Le^b$ only on PSGL-1/$mIgG_{2b}$—a fusion protein carrying almost only O-glycans (FIG. 6). Further, only 2C2 cells, and not 1C5 cells, expressed $Le^b$ on glycosphingolipids isolated from the respective cell lines (FIG. 7)/

EXAMPLE 8

Figure 8:
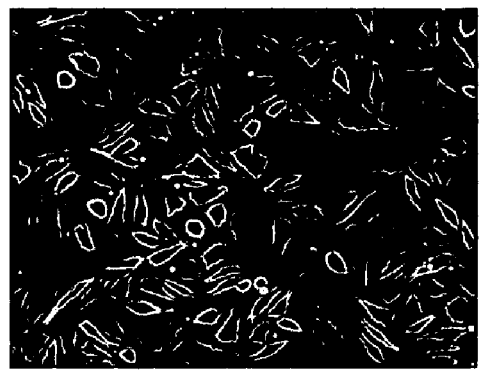
FIG. 8 are a series of photographs showing fixed monolayers of CHO-K1, 1C5 and 2C2 were incubated with the FITC-labelled, Le$^b$-binding H. pylori strain, 17875/Le$^b$, washed and inspected by fluorescence microscopy.
Figure 8:
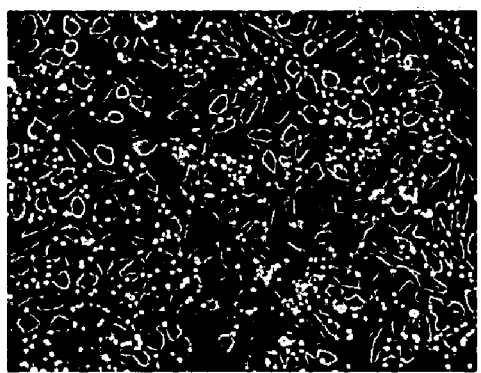
Figure 8:
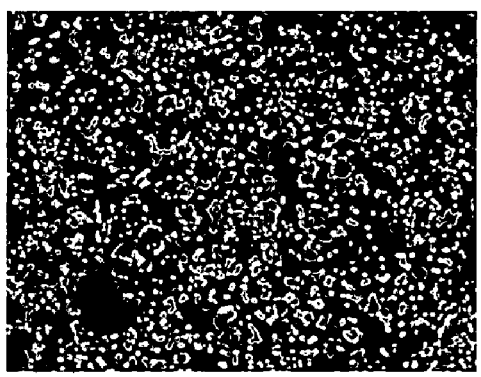
Figure 9:
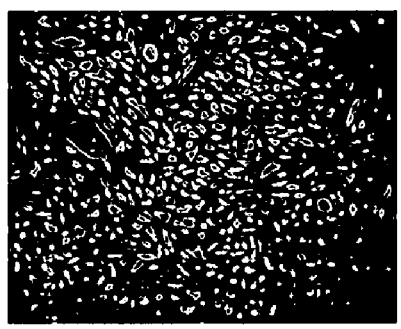
FIG. 9 are a series of photographs showing fixed monolayers of CHO-K1, 1C5 and 2C2 were incubated with the FITC-labelled, Le$^b$-binding H. pylori strain, 17875/Le$^b$, washed and inspected by fluorescence microscopy.
Figure 9:
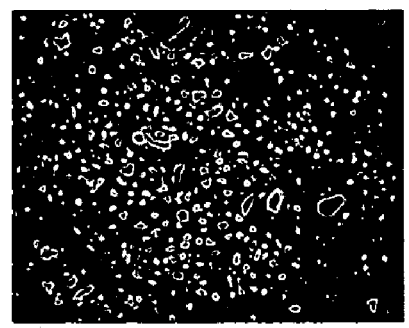
Figure 9:
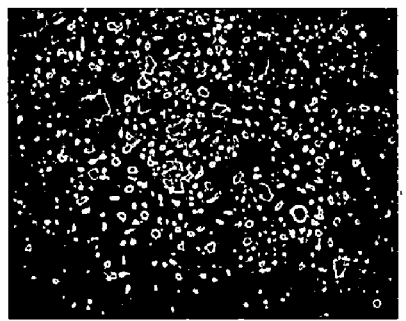
Figure 9:
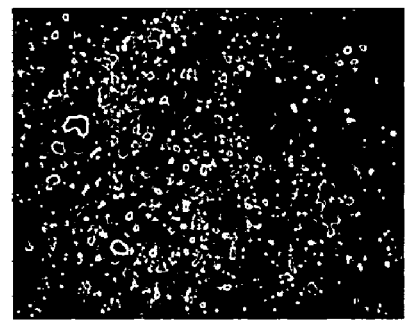
Figure 9:
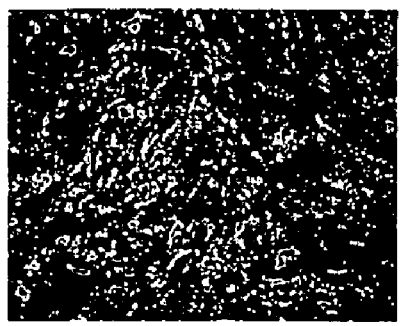
Figure 9:
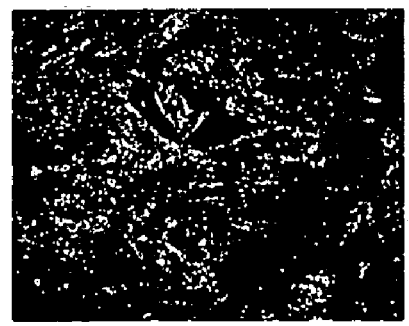

Attachment Of *H. Pylori* Via Baba Is Dependent On $Le^B$ Expression, But Independent Of The Glycan Type Carrying $Le^B$ The $Le^b$-binding *H. pylori* strain, 17875/$Le^b$, attached to both $Le^b$-expressing clones albeit in higher numbers to the 2C2 clone (FIGS. 8 and 9). No binding was seen with this *H. pylori* strain to the parental CHO-K1 cells (FIGS. 8 and 9), or $Le^a$- and H type 1-expressing cells.

REFERENCES

1. Ilver, D., Arnqvist, A., Ogren, J., Frick, I. M., Kersulyte, D., Incecik, E. T., Berg, D. E., Covacci, A., Engstrand, L., and Boren, T. (1998) in *Science* Vol. 279, pp. 373-377
2. Mahdavi, J., Sonden, B., Hurtig, M., Olfat, F. O., Forsberg, L., Roche, N., Angstrom, J., Larsson, T., Teneberg, S., Karlsson, K. A., Altraja, S., Wadstrom, T., Kersulyte, D., Berg, D. E., Dubois, A., Petersson, C., Magnusson, K. E., Norberg, T., Lindh, F., Lundskog, B. B., Arnqvist, A., Hammarstrom, L., and Boren, T. (2002) in *Science* Vol. 297, pp. 573-578
3. Gerhard, M., Lehn, N., Neumayer, N., Boren, T., Rad, R., Schepp, W., Miehlke, S., Classen, M., and Prinz, C. (1999) in *Proc Natl Acad Sci USA* Vol. 96, pp. 12778-12783
4. Rad, R., Gerhard, M., Lang, R., Schoniger, M., Rosch, T., Schepp, W., Becker, I., Wagner, H., and Prinz, C. (2002) in *J Immunol* Vol. 168, pp. 3033-3041
5. Prinz, C., Schoniger, M., Rad, R., Becker, I., Keiditsch, E., Wagenpfeil, S., Classen, M., Rosch, T., Schepp, W., and Gerhard, M. (2001) in *Cancer Res* Vol. 61, pp. 1903-1909
6. Guruge, J. L., Falk, P. G., Lorenz, R. G., Dans, M., Wirth, H. P., Blaser, M. J., Berg, D. E., and Gordon, J. I. (1998) in *Proc Natl Acad Sci USA* Vol. 95, pp. 3925-3930
7. Takahashi, T., Matsumoto, T., Nakamura, M., Matsui, H., Kiyohara, H., Sasakawa, C., and Yamada, H. (2004) in *Helicobacter* Vol. 9, pp. 302-312
8. Amado, M., Almeida, R., Carneiro, F., Levery, S. B., Holmes, E, H., Nomoto, M., Hollingsworth, M. A., Hassan, H., Schwientek, T., Nielsen, P. A., Bennett, E. P., and Clausen, H. (1998) *J Biol Chem* 273, 12770-12778
9. Isshiki, S., Togayachi, A., Kudo, T., Nishihara, S., Watanabe, M., Kubota, T., Kitajima, M., Shiraishi, N., Sasaki, K., Andoh, T., and Narimatsu, H. (1999) in *J Biol Chem* Vol. 274, pp. 12499-12507
10. Cole, S. E., Mao, M. S., Johnston, S. H., and Vogt, T. F. (2001) *Mamm Genome* 12, 177-179
11. Mare, L., and Trinchera, M. (2004) in *Eur J Biochem* Vol. 271, pp. 186-194
12. Kolbinger, F., Streiff, M. B., and Katopodis, A. G. (1998) in *J Biol Chem Vol.* 273, pp. 433-440
13. Iwai, T., Inaba, N., Naundorf, A., Zhang, Y., Gotoh, M., Iwasaki, H., Kudo, T., Togayachi, A., Ishizuka, Y., Nakanishi, H., and Narimatsu, H. (2002) in *J Biol Chem* Vol. 277, pp. 12802-12809
14. Prieto, P. A., Larsen, R. D., Cho, M., Rivera, H. N., Shilatifard, A., Lowe, J. B., Cummings, R. D., and Smith, D. F. (1997) in *J Biol Chem* Vol. 272, pp. 2089-2097
15. Lofling, J. C., Hauzenberger, E., and Holgersson, J. (2002) *Absorption of anti-blood group A antibodies on P-selectin glycoprotein ligand-1/immunoglobulin chimeras carrying blood group A determinants: core saccharide chain specificity of the Se and H gene encoded alpha1,2fucosyltransferases in different host cells.* Glycobiology, 12
16. Narimatsu, H., Iwasaki, H., Nakayama, F., Ikehara, Y., Kudo, T., Nishihara, S., Sugano, K., Okura, H., Fujita, S., and Hirohashi, S. (1998) in *Cancer Res* Vol. 58, pp. 512-518
17. Narimatsu, H., Iwasaki, H., Nishihara, S., Kimura, H., Kudo, T., Yamauchi, Y., and Hirohashi, S. (1996) in *Cancer Res* Vol. 56, pp. 330-338
18. Mahdavi, J., Sonden, B., Hurtig, M., Olfat, F. O., Forsberg, L., Roche, N., Angstrom, J., Larsson, T., Teneberg, S., Karlsson, K. A., Altraja, S., Wadstrom, T., Kersulyte, D., Berg, D. E., Dubois, A., Petersson, C., Magnusson, K. E., Norberg, T., Lindh, F., Lundskog, B. B., Arnqvist, A., Hammarstrom, L., and Boren, T. (eds) (2002) *Helicobacterpylori SabA adhesin in persistent infection and chronic inflammation* Vol. 297. Science
19. Ilver, D., Arnqvist, A., Ogren, J., Frick, I. M., Kersulyte, D., Incecik, E. T., Berg, D. E., Covacci, A., Engstrand, L., and Boren, T. (1998) in *Science* Vol. 279, pp. 373-377

20. Iwai, T., Inaba, N., Naundorf, A., Zhang, Y., Gotoh, M., Iwasaki, H., Kudo, T., Togayachi, A., Ishizuka, Y., Nakanishi, H., and Narimatsu, H. (2002) *J Biol Chem* 277, 12802-12809
21. Zhou, D., Berger, E. G., and Hennet, T. (1999) *Eur J Biochem* 263, 571-576
22. Kelly, R. J., Rouquier, S., Giorgi, D., Lennon, G. G., and Lowe, J. B. (1995) *J Biol Chem* 270, 4640-4649
23. Lofling, J. C., Hauzenberger, E., and Holgersson, J. (2002) *Glycobiology* 12, 173-182
24. Kukowska-Latallo, J. F., Larsen, R. D., Nair, R. P., and Lowe, J. B. (1990) *Genes Dev* 4, 1288-1303
25. Amano, J., and Oshima, M. (1999) in *J Biol Chem* Vol. 274, pp. 21209-21216
26. Falk, P. G., Bry, L., Holgersson, J., and Gordon, J. I. (1995) in *Proc Natl Acad Sci USA* Vol. 92, pp. 1515-1519
27. Bergman, M. P., Engering, A., Smits, H. H., van Vliet, S. J., van Bodegraven, A. A., Wirth, H. P., Kapsenberg, M. L., Vandenbroucke-Grauls, C. M., van Kooyk, Y., and Appelmelk, B. J. (2004) in *J Exp Med* Vol. 200, pp. 979-990
28. Appelmelk, B. J., van Die, I., van Vliet, S. J., Vandenbroucke-Grauls, C. M., Geijtenbeek, T. B., and van Kooyk, Y. (2003) in *J Immunol* Vol. 170, pp. 1635-1639
29. Kotani, N., Asano, M., Iwakura, Y., and Takasaki, S. (2001) in *Biochem J* Vol. 357, pp. 827-834

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion polypeptide comprising a first polypeptide operably linked to a second polypeptide, wherein the first polypeptide is glycosylated
   a. on O-linked glycans by an α1,¾ fucosyltransferase, an α1,2 fucosyltransferase, a β1,3 galactosyltransferase and a β 1,3, N-acetylglucosaminyltransferase, or
   b. on N-linked glycans by an α1,¾ fucosyltransferase, an α1,2 fucosyltransferase and a β1,3 galactosyltransferase; and
   c. comprises multiple Le$^b$ epitopes;

and the second polypeptide comprises at least a region of an immunoglobulin polypeptide.

2. The fusion polypeptide of claim 1, wherein the first polypeptide is a mucin polypeptide.

3. The fusion polypeptide of claim 1, wherein said mucin polypeptide comprises at least a region of a P-selectin glycoprotein ligand-1.

4. The fusion polypeptide of claim 2, wherein said mucin polypeptide includes an extracellular portion of a P-selectin glycoprotein ligand-1.

5. The fusion polypeptide of claim 1, wherein the first polypeptide is a glycoprotein.

6. The fusion polypeptide of claim 5, wherein the glycoprotein carries N-linked glycans.

7. The fusion polypeptide of claim 1, wherein the first polypeptide is an alpha-1 glycoprotein polypeptide.

8. The fusion polypeptide of claim 1, wherein the first polypeptide comprises at least a region of an alpha-1-acid glycoprotein.

9. The fusion polypeptide of claim 1, wherein the second polypeptide comprises a region of a heavy chain immunoglobulin polypeptide.

10. The fusion polypeptide of claim 1, wherein said second polypeptide comprises an Fc region of an immunoglobulin heavy chain.

11. The fusion polypeptide of claim 1, wherein the fusion polypeptide is a dimer.

12. An inhibitor of microbial adhesion comprising the fusion polypeptide of claim 1.

* * * * *

UNITED STATES PATENT AND TRADEMARK OFFICE
CERTIFICATE OF CORRECTION

| | | |
|---|---|---|
| PATENT NO. | : 7,658,919 B2 | Page 1 of 1 |
| APPLICATION NO. | : 11/251140 | |
| DATED | : February 9, 2010 | |
| INVENTOR(S) | : Holgersson et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 231 days.

Delete the phrase "by 231 days" and insert -- by 627 days --

Signed and Sealed this

First Day of June, 2010

David J. Kappos
*Director of the United States Patent and Trademark Office*